(12) United States Patent
Itskovitz-Eldor et al.

(10) Patent No.: US 8,927,274 B2
(45) Date of Patent: Jan. 6, 2015

(54) POPULATIONS OF PANCREATIC PROGENITOR CELLS AND METHODS OF ISOLATING AND USING SAME

(75) Inventors: Joseph Itskovitz-Eldor, Haifa (IL); Bettina Fishman, Haifa (IL); Hanna Segev, Moshav Hogla (IL)

(73) Assignee: Technion Research & Development Foundation Limited, Haifa (IL)

( * ) Notice: Subject to any disclaimer, the term of this patent is extended or adjusted under 35 U.S.C. 154(b) by 0 days.

(21) Appl. No.: 13/640,532

(22) PCT Filed: Apr. 12, 2011

(86) PCT No.: PCT/IL2011/000302
§ 371 (c)(1),
(2), (4) Date: Oct. 11, 2012

(87) PCT Pub. No.: WO2011/128897
PCT Pub. Date: Oct. 20, 2011

(65) Prior Publication Data
US 2013/0034526 A1 Feb. 7, 2013

Related U.S. Application Data

(60) Provisional application No. 61/322,942, filed on Apr. 12, 2010.

(51) Int. Cl.
*A61K 35/39* (2006.01)
*A61K 35/12* (2006.01)
*C12N 5/071* (2010.01)
*A61P 3/10* (2006.01)
*A61K 38/28* (2006.01)
*A61K 38/00* (2006.01)

(52) U.S. Cl.
CPC .............. *C12N 5/0678* (2013.01); *A61K 38/00* (2013.01); *C12N 2506/02* (2013.01); *C12N 2506/45* (2013.01)
USPC ........... 435/366; 435/377; 424/93.7; 514/6.7; 514/6.9

(58) Field of Classification Search
None
See application file for complete search history.

(56) References Cited

U.S. PATENT DOCUMENTS

| 5,744,327 A * | 4/1998 | Newgard ..................... 435/69.4 |
| 2006/0040385 A1 * | 2/2006 | Itskovitz-Eldor et al. ..... 435/366 |
| 2007/0259423 A1 * | 11/2007 | Odorico et al. ............... 435/366 |

FOREIGN PATENT DOCUMENTS

WO WO 02092756 A2 * 11/2002
WO WO 2004/050827 6/2004

OTHER PUBLICATIONS

Jiang, W., et al. "In vitro derivation of functional insulin-producing cells from human embryonic stem cells," Cell Research 17:333-344 (Apr. 10, 2007).*
Segev, H., et al. "Differentiation of Human Embryonic Stem Cells into Insulin-Producing Clusters," Stem Cells 22:265-274 (2004).*
Bain, J.R., et al. "An adenovirus vector for efficient RNA interference-mediated suppression of target genes in insulinoma cells and pancreatic islets of Langerhans," Diabetes 53:2190-2194 (2004).*
Leturque, A., et al. "GLUT2 mutations, translocation, and receptor function in diet sugar managing," Am J Physiol Endocrinol Metab 296: E985-E992 (Feb. 17, 2009).*
Zhang, D., et al. "Highly efficient differentiation of human ES cells and iPS cells into mature pancreatic insulin-producing cells," Cell Research 19:429-438 (Mar. 3, 2009).*
Cleveland Clinic "Blood Glucose Test", Cleveland Clinic Health Information, retrieved from <URL:http://my.clevelandclinic.org/services/blood_glucose_test/hic_blood_glucose_test.aspx>, archived online Sep. 16, 2008, 2 pages.*
Tomlinson et al "Cell separation: Terminology and practical considerations" J Tiss. Eng., 2013 (published online Dec. 28, 2012), 3(1), pp. 1-14.*
Kazuaki Ohtsubo; Shinji Takamatsu; Mari T. Minowa; Aruto Yoshida; Makoto Takeuchi; and Jamey D. Marth "Dietary and Genetic Control of Glucose Transporter 2 Glycosylation Promotes Insulin Secretion in Suppressing Diabetes" Cell 2005 (Dec. 29), 123, 1307-1321.*
International Preliminary Report on Patentability Dated Oct. 26, 2012 From the International Bureau of WIPO Re. Application No. PCT/IL2011/000302.
International Search Report and the Written Opinion Dated Jul. 29, 2011 From the International Searching Authority Re. Application No. PCT/IL2011/000302.
Chen et al. "A Small Molecule That Directs Differentiation of Human Embryonic Stem Cells Into the Pancreatic Lineage: Supplementary Material", Nature Chemical Biology, 21 P.
Chen et al. "A Small Molecule That Directs Differentiation of Human ESCs Into the Pancreatic Lineage", Nature Chemical Biology, 5(4): 258-265, Apr. 2009.
Frandsen et al. "Activin B Mediated Induction of Pdx1 in Human Embryonic Stem Cell Derived Embryoid Bodies", Biochemical and Biophysical Research Communications, 2007.
Maehr et al. "Generation of Pluripotent Stem Cells From Patients With Type 1 Diabetes", Proc. Natl. Acad. Sci. USA, 106(37): 15768-15773, Sep. 15, 2009.

(Continued)

*Primary Examiner* — Chris R Tate
*Assistant Examiner* — Aaron J Kosar

(57) ABSTRACT

A method of generating pancreatic progenitor cells is disclosed. The method comprises:
(a) differentiating stem cells under conditions such that at least a portion of the cells express glucose transporter 2 (GLUT2) so as to generate GLUT2-expressing cells; and
(b) enriching for the GLUT2-expressing cells so as to generate a population of GLUT2 enriched cells, wherein at least 80% of the population of GLUT2 enriched cells express GLUT2, thereby generating pancreatic progenitor cells.

Isolated populations of cells generated according to the method, pharmaceutical compositions comprising same and uses thereof are also disclosed.

12 Claims, 13 Drawing Sheets
(12 of 13 Drawing Sheet(s) Filed in Color)

(56) References Cited

OTHER PUBLICATIONS

Shim et al. "Directed Differentiation of Human Embryonic Stem Cells Towards a Pancreatic Cell Fate", Diabetologia, 11 P., Jan. 15, 2007.

Sugiyama et al. "Conserved Markers of Fetal Pancreatic Epithelium Permit Prospective Isolation of Islet Progenitor Cells by FACS", Proc. Natl. Acad. Sci. USA, PNAS, 104(1): 175-180, Jan. 2, 2007.

Tateishi et al. "Generation of Insulin-Secreting Islet-Like Clusters From Human Skin Fibroblasts", The Journal of Biological Chemistry, 283(46): 31601-31607, Nov. 14, 2008.

Tonack et al. "Differential Expression of Glucose Transporter Isoforms During Embryonic Stem Cell Differentiation", Differentiation, 74: 499-509, 2006.

International Search Report and the Written Opinion Dated Jul. 29, 2011 From the International Searching Authority Re. Application No. PCT/IL2011/000302, 14 pages.

Borowiak et al. "Small Molecules Efficiently Direct Endodermal Differentiation of Mouse and Human Embryonic Stem Cells", Cell Stem Cell, 4: 348-358, Apr. 3, 2009.

Chen et al. "A Small Molecule That Directs Differentiation of Human Embryonic Stem Cells Into the Pancreatic Lineage", Nature Chemical Biology, Apr. 2009, 5 ( 4 ), pp. 258-265 and Supp. Mater. S1-S21.

D'Amour et al. "Production of Pancreatic Hormone-Expressing Endocrine Cells From Human Embryonic Stem Cells", Nature Biotechnology, p. 1-10, Published Online Oct. 19, 2006.

D'Amour et al. "Production of Pancreatic Hormone-Expressing Endocrine Cells From Human Embryonic Stem Cells", Nature Biotechnology, 24(11): 1392-1401, Jan. 1, 2006.

Frandsen et al. "Activin B Mediated Induction of Pdx1 in Human Embryonic Stem Cell Derived Embryoid Bodies", Biochemical and Biophysical Research Communications, 2007, 7 pages.

Jiang et al. "Generation of Insulin-Producing Islet-Like Clusters From Human Embryonic Stem Cells", Stem Cells, 23 P., May 19, 2007.

Jiang et al. "In Vitro Derivation of Functional Insulin-Producing Cells From Human Embryonic Stem Cells", Cell Research, 17(4): 333-344, Apr. 10, 2007.

Johannesson et al. "FGF4 and Retinoic Acid Direct Differentiation of hESCs Into PDX1-Expressing Foregut Endoderm in a Time- and Concentration-Dependent Manner", PLoS ONE, 4(3/e4794): 1-13, Mar. 2009.

Kroon et al. "Pancreatic Endoderm Derived From Human Embryonic Stem Cells Generates Glucose-Reponsive Insulin-Secreting Cells in Vivo", Nature Biotechnology, p. 1-10, Advance Online Publication, 2008.

Liew et al. "Stem Cell Therapy to Treat Diabetes Mellitus", the Review of Diabetic Study, RDS, 5(4): 203-219, Jan. 2008.

Maehr et al. "Generation of Pluripotent Stem Cells From Patients With Type 1 Diabetes", Proc. Natl. Acad. Sci. USA 106(37): 15768-15773, Sep. 15, 2009.

Naujok et al. "Changes in Gene Expression and Morphology of Mouse Embryonic Stem Cells on Differentiation Into Insulin-Producing Cells In Vitro and In Vivo", Diabetes/Metabolism Research and Reviews, 25(5): 464-476, Jul. 1, 2009.

Piper et al. "Beta Cell Differentiation During Early Human Pancreas Development", Journal of Endocrinology, 181: 11-23, 2004.

Piper et al. "Beta-Cell Differentiation During Human Development Does Not Rely on Nestin-Positive Precursors: Implications for Stem Cell-Derived Replacement Therapy", Diabetologia, 45: 1045-1047, Mar. 18, 2002.

Segev et al. "Differentiation of Human Embryonic Stem Cells Into Insulin-Producing Clusters", Stem Cells, 22(3): 265-274, Jan. 1, 2004.

Semb "Expandable Endodermal Progenitors: New Tools to Explore Endoderm and Its Derivatives", Cell Stem Cell, 3: 355-356, Oct. 9, 2008.

\* cited by examiner

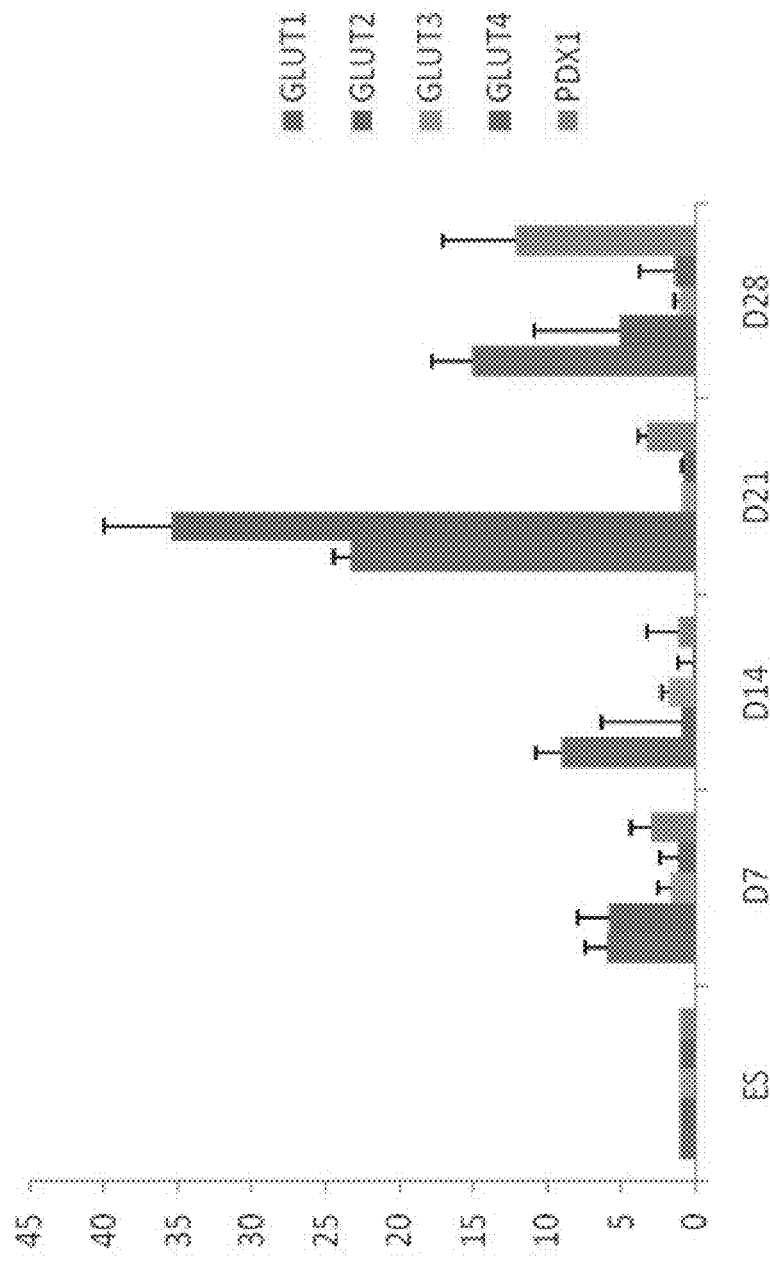

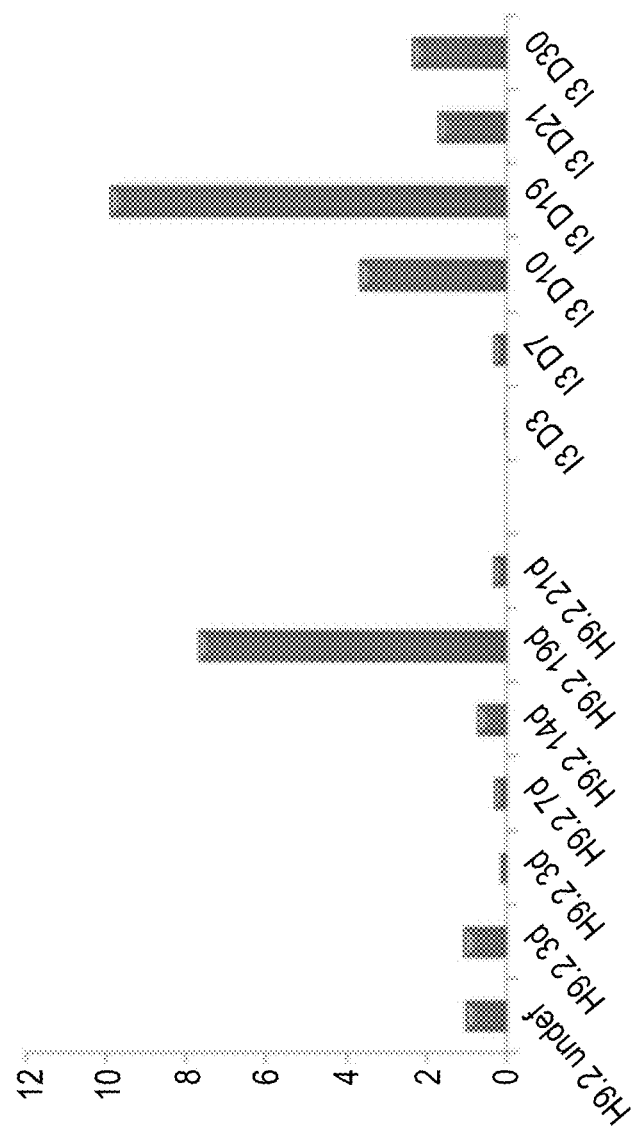

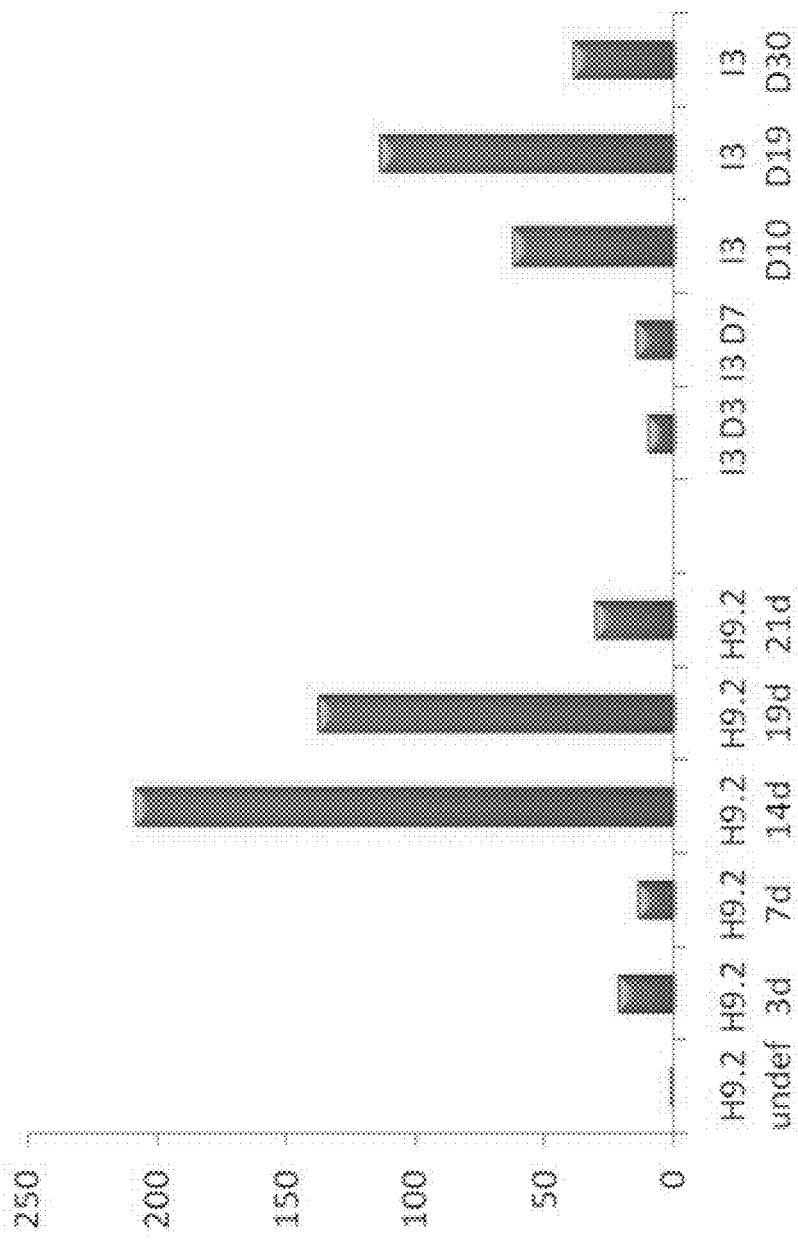

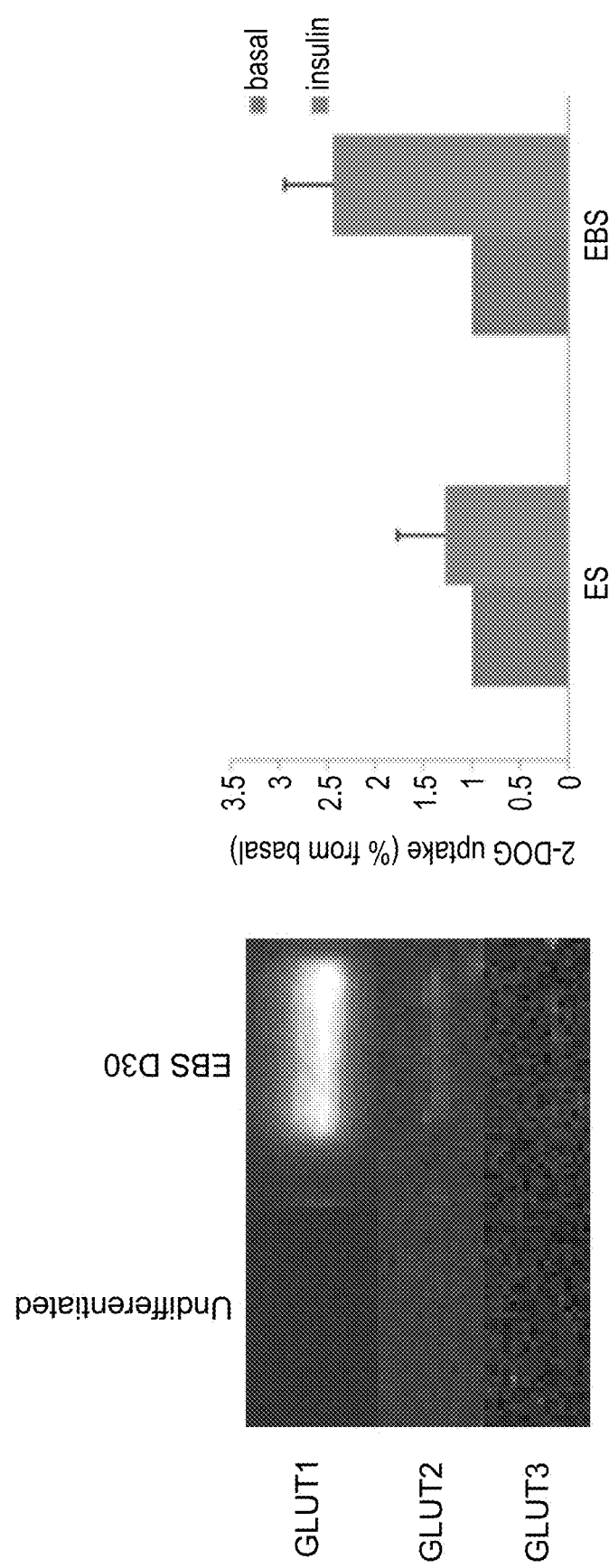

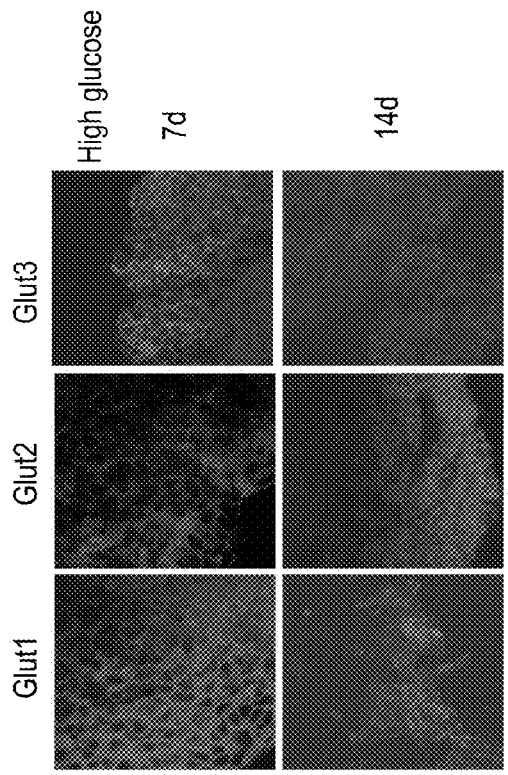
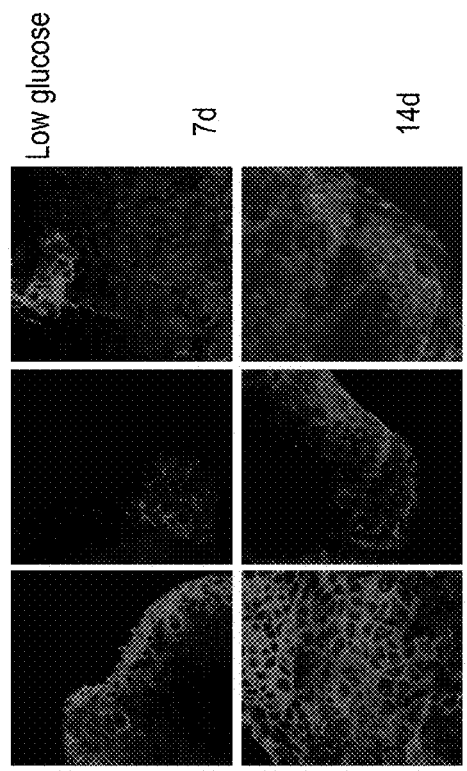
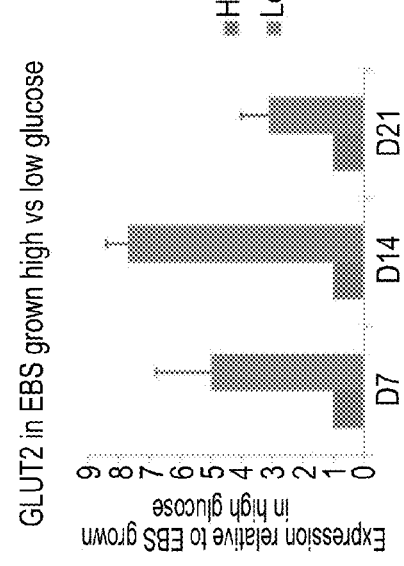
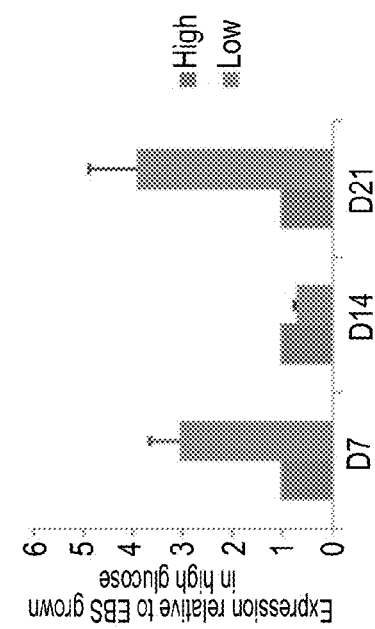
FIG. 2A
FIG. 2B
FIG. 2C

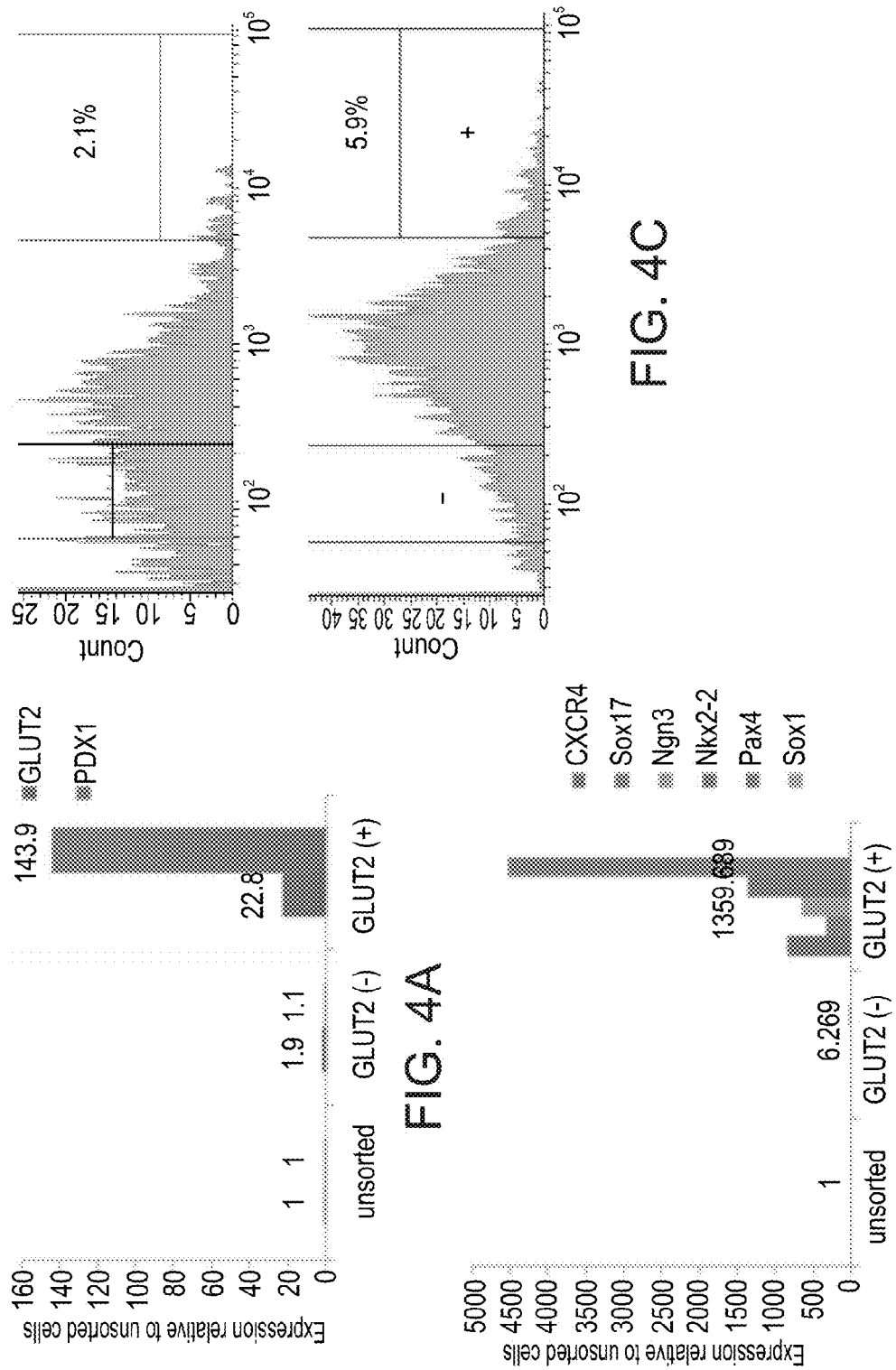

SEQUENCE LISTING

```
<160> NUMBER OF SEQ ID NOS: 40

<210> SEQ ID NO 1
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 1
ggcgcagcag aatccaga                                                 18

<210> SEQ ID NO 2
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 2
ccacgacttg cccagcat                                                 18

<210> SEQ ID NO 3
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 3
caccgcatct ggagaacca                                                19
```

```
<210> SEQ ID NO 4
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 4
gcccatttcc tcggtgtagt t                                              21

<210> SEQ ID NO 5
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 5
aagtctacca aagctcacgc g                                              21

<210> SEQ ID NO 6
<211> LENGTH: 15
<212> TYPE: DNA
<213> ORGANISM: Artificial sequence
<220> FEATURE:
<223> OTHER INFORMATION: Single strand DNA oligonucleotide

<400> SEQUENCE: 6
gtaggcgccg cctgc                                                     15

<210> SEQ ID NO 7
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 7
gctcatcgct ctctattctt ttgc                                           24

<210> SEQ ID NO 8
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 8
ggttgaggcg tcatcctttc t                                              21

<210> SEQ ID NO 9
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 9
gggtctggtt ttccaacaga ag                                             22

<210> SEQ ID NO 10
<211> LENGTH: 17
<212> TYPE: DNA
<213> ORGANISM: Artificial sequence
<220> FEATURE:
<223> OTHER INFORMATION: Single strand DNA oligonucleotide
```

```
<400> SEQUENCE: 10
tcagcccctg ggaagca                                                    17

<210> SEQ ID NO 11
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 11
ggccttcagt actccctgca                                                 20

<210> SEQ ID NO 12
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 12
gggacttgga gcttgagtcc t                                               21

<210> SEQ ID NO 13
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 13
atgcaccgct acgacatgg                                                  19

<210> SEQ ID NO 14
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 14
ctcatgtagc cctgcgagtt g                                               21

<210> SEQ ID NO 15
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 15
aggacttctg tggaccttat gtg                                             23

<210> SEQ ID NO 16
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 16
gttcatgtca aaaagcaggg                                                 20
```

```
<210> SEQ ID NO 17
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 17
atactcatga ccatcgcgct ag                                                  22

<210> SEQ ID NO 18
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 18
aaagaaggcc acaaagccaa atg                                                 23

<210> SEQ ID NO 19
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 19
actttgacgg acaagggaaa tg                                                  22

<210> SEQ ID NO 20
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 20
accagtgaca gccaacagg                                                      19

<210> SEQ ID NO 21
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 21
gggagcggtg aagatgga                                                       18

<210> SEQ ID NO 22
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 22
tcatgttgct cacggaggag ta                                                  22

<210> SEQ ID NO 23
<211> LENGTH: 21
<212> TYPE: DNA
<213> ORGANISM: Artificial sequence
<220> FEATURE:
<223> OTHER INFORMATION: Single strand DNA oligonucleotide
```

```
<400> SEQUENCE: 23
ttccaacagt aggctccgaa g                                              21

<210> SEQ ID NO 24
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 24
aagcaccgca gagaacacag                                                20

<210> SEQ ID NO 25
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 25
taccaccaca cccatca                                                   17

<210> SEQ ID NO 26
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 26
acaccaagac agggaca                                                   17

<210> SEQ ID NO 27
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 27
ctcaccctgg gggttctat                                                 19

<210> SEQ ID NO 28
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 28
ctccaggttg cctctctcac t                                              21

<210> SEQ ID NO 29
<211> LENGTH: 14
<212> TYPE: DNA
<213> ORGANISM: Artificial sequence
<220> FEATURE:
<223> OTHER INFORMATION: Single strand DNA oligonucleotide

<400> SEQUENCE: 29
tgagtgtgga tcca                                                      14
```

-continued

```
<210> SEQ ID NO 30
<211> LENGTH: 14
<212> TYPE: DNA
<213> ORGANISM: Artificial sequence
<220> FEATURE:
<223> OTHER INFORMATION: Single strand DNA oligonucleotide

<400> SEQUENCE: 30
tgaataagca gatc                                                        14

<210> SEQ ID NO 31
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 31
ccacatcgct cagaaccat                                                   19

<210> SEQ ID NO 32
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 32
ggcaacaata tccatttacc ag                                               22

<210> SEQ ID NO 33
<211> LENGTH: 356
<212> TYPE: PRT
<213> ORGANISM: Homo sapiens

<400> SEQUENCE: 33

Met Thr Lys Ser Tyr Ser Glu Ser Gly Leu Met Gly Glu Pro Gln Pro
1               5                   10                  15

Gln Gly Pro Pro Ser Trp Thr Asp Glu Cys Leu Ser Ser Gln Asp Glu
            20                  25                  30

Glu His Glu Ala Asp Lys Lys Glu Asp Asp Leu Glu Ala Met Asn Ala
        35                  40                  45

Glu Glu Asp Ser Leu Arg Asn Gly Gly Glu Glu Glu Asp Glu Asp Glu
    50                  55                  60

Asp Leu Glu Glu Glu Glu Glu Glu Glu Asp Asp Asp Gln Lys
65                  70                  75                  80

Pro Lys Arg Arg Gly Pro Lys Lys Lys Met Thr Lys Ala Arg Leu
                85                  90                  95

Glu Arg Phe Lys Leu Arg Arg Met Lys Ala Asn Ala Arg Glu Arg Asn
            100                 105                 110

Arg Met His Gly Leu Asn Ala Ala Leu Asp Asn Leu Arg Lys Val Val
        115                 120                 125

Pro Cys Tyr Ser Lys Thr Gln Lys Leu Ser Lys Ile Glu Thr Leu Arg
    130                 135                 140

Leu Ala Lys Asn Tyr Ile Trp Ala Leu Ser Glu Ile Ser Arg Ser Gly
145                 150                 155                 160

Lys Ser Pro Asp Leu Val Ser Phe Val Gln Thr Leu Cys Lys Gly Leu
                165                 170                 175

Ser Gln Pro Thr Thr Asn Leu Val Ala Gly Cys Leu Gln Leu Asn Pro
            180                 185                 190
```

Arg Thr Phe Leu Pro Glu Gln Asn Gln Asp Met Pro His Leu Pro
        195                 200                 205

Thr Ala Ser Ala Ser Phe Pro Val His Pro Tyr Ser Tyr Gln Ser Pro
210                 215                 220

Gly Leu Pro Ser Pro Pro Tyr Gly Thr Met Asp Ser Ser His Val Phe
225                 230                 235                 240

His Val Lys Pro Pro His Ala Tyr Ser Ala Ala Leu Glu Pro Phe
        245                 250                 255

Phe Glu Ser Pro Leu Thr Asp Cys Thr Ser Pro Ser Phe Asp Gly Pro
        260                 265                 270

Leu Ser Pro Pro Leu Ser Ile Asn Gly Asn Phe Ser Phe Lys His Glu
        275                 280                 285

Pro Ser Ala Glu Phe Glu Lys Asn Tyr Ala Phe Thr Met His Tyr Pro
290                 295                 300

Ala Ala Thr Leu Ala Gly Ala Gln Ser His Gly Ser Ile Phe Ser Gly
305                 310                 315                 320

Thr Ala Ala Pro Arg Cys Glu Ile Pro Ile Asp Asn Ile Met Ser Phe
                325                 330                 335

Asp Ser His Ser His His Glu Arg Val Met Ser Ala Gln Leu Asn Ala
                340                 345                 350

Ile Phe His Asp
        355

<210> SEQ ID NO 34
<211> LENGTH: 422
<212> TYPE: PRT
<213> ORGANISM: Homo sapiens

<400> SEQUENCE: 34

Met Gln Asn Ser His Ser Gly Val Asn Gln Leu Gly Gly Val Phe Val
1               5                   10                  15

Asn Gly Arg Pro Leu Pro Asp Ser Thr Arg Gln Lys Ile Val Glu Leu
            20                  25                  30

Ala His Ser Gly Ala Arg Pro Cys Asp Ile Ser Arg Ile Leu Gln Val
        35                  40                  45

Ser Asn Gly Cys Val Ser Lys Ile Leu Gly Arg Tyr Tyr Glu Thr Gly
    50                  55                  60

Ser Ile Arg Pro Arg Ala Ile Gly Gly Ser Lys Pro Arg Val Ala Thr
65                  70                  75                  80

Pro Glu Val Val Ser Lys Ile Ala Gln Tyr Lys Arg Glu Cys Pro Ser
                85                  90                  95

Ile Phe Ala Trp Glu Ile Arg Asp Arg Leu Leu Ser Glu Gly Val Cys
            100                 105                 110

Thr Asn Asp Asn Ile Pro Ser Val Ser Ser Ile Asn Arg Val Leu Arg
        115                 120                 125

Asn Leu Ala Ser Glu Lys Gln Gln Met Gly Ala Asp Gly Met Tyr Asp
    130                 135                 140

Lys Leu Arg Met Leu Asn Gly Gln Thr Gly Ser Trp Gly Thr Arg Pro
145                 150                 155                 160

Gly Trp Tyr Pro Gly Thr Ser Val Pro Gly Gln Pro Thr Gln Asp Gly
                165                 170                 175

Cys Gln Gln Gln Glu Gly Gly Gly Glu Asn Thr Asn Ser Ile Ser Ser
            180                 185                 190

Asn Gly Glu Asp Ser Asp Glu Ala Gln Met Arg Leu Gln Leu Lys Arg
        195                 200                 205

```
Lys Leu Gln Arg Asn Arg Thr Ser Phe Thr Gln Glu Gln Ile Glu Ala
210                 215                 220

Leu Glu Lys Glu Phe Glu Arg Thr His Tyr Pro Asp Val Phe Ala Arg
225                 230                 235                 240

Glu Arg Leu Ala Ala Lys Ile Asp Leu Pro Glu Ala Arg Ile Gln Val
            245                 250                 255

Trp Phe Ser Asn Arg Arg Ala Lys Trp Arg Arg Glu Glu Lys Leu Arg
            260                 265                 270

Asn Gln Arg Arg Gln Ala Ser Asn Thr Pro Ser His Ile Pro Ile Ser
            275                 280                 285

Ser Ser Phe Ser Thr Ser Val Tyr Gln Pro Ile Pro Gln Pro Thr Thr
290                 295                 300

Pro Val Ser Ser Phe Thr Ser Gly Ser Met Leu Gly Arg Thr Asp Thr
305                 310                 315                 320

Ala Leu Thr Asn Thr Tyr Ser Ala Leu Pro Met Pro Ser Phe Thr
            325                 330                 335

Met Ala Asn Asn Leu Pro Met Gln Pro Pro Val Pro Ser Gln Thr Ser
            340                 345                 350

Ser Tyr Ser Cys Met Leu Pro Thr Ser Pro Ser Val Asn Gly Arg Ser
            355                 360                 365

Tyr Asp Thr Tyr Thr Pro Pro His Met Gln Thr His Met Asn Ser Gln
            370                 375                 380

Pro Met Gly Thr Ser Gly Thr Thr Ser Thr Gly Leu Ile Ser Pro Gly
385                 390                 395                 400

Val Ser Val Pro Val Gln Val Pro Gly Ser Glu Pro Asp Met Ser Gln
                405                 410                 415

Tyr Trp Pro Arg Leu Gln
            420

<210> SEQ ID NO 35
<211> LENGTH: 343
<212> TYPE: PRT
<213> ORGANISM: Homo sapiens

<400> SEQUENCE: 35

Met Asn Gln Leu Gly Gly Leu Phe Val Asn Gly Arg Pro Leu Pro Leu
1               5                   10                  15

Asp Thr Arg Gln Gln Ile Val Arg Leu Ala Val Ser Gly Met Arg Pro
            20                  25                  30

Cys Asp Ile Ser Arg Ile Leu Lys Val Ser Asn Gly Cys Val Ser Lys
        35                  40                  45

Ile Leu Gly Arg Tyr Tyr Arg Thr Gly Val Leu Glu Pro Lys Gly Ile
    50                  55                  60

Gly Gly Ser Lys Pro Arg Leu Ala Thr Pro Val Val Ala Arg Ile
65                  70                  75                  80

Ala Gln Leu Lys Gly Glu Cys Pro Ala Leu Phe Ala Trp Glu Ile Gln
                85                  90                  95

Arg Gln Leu Cys Ala Glu Gly Leu Cys Thr Gln Asp Lys Thr Pro Ser
            100                 105                 110

Val Ser Ser Ile Asn Arg Val Leu Arg Ala Leu Gln Glu Asp Gln Gly
            115                 120                 125

Leu Pro Cys Thr Arg Leu Arg Ser Pro Ala Val Leu Ala Pro Ala Val
130                 135                 140

Leu Thr Pro His Ser Gly Ser Glu Thr Pro Arg Gly Thr His Pro Gly
145                 150                 155                 160
```

```
Thr Gly His Arg Asn Arg Thr Ile Phe Ser Pro Ser Gln Ala Glu Ala
            165                 170                 175

Leu Glu Lys Glu Phe Gln Arg Gly Gln Tyr Pro Asp Ser Val Ala Arg
        180                 185                 190

Gly Lys Leu Ala Thr Ala Thr Ser Leu Pro Glu Asp Thr Val Arg Val
            195                 200                 205

Trp Phe Ser Asn Arg Arg Ala Lys Trp Arg Arg Gln Glu Lys Leu Lys
        210                 215                 220

Trp Glu Met Gln Leu Pro Gly Ala Ser Gln Gly Leu Thr Val Pro Arg
225                 230                 235                 240

Val Ala Pro Gly Ile Ile Ser Ala Gln Gln Ser Pro Gly Ser Val Pro
            245                 250                 255

Thr Ala Ala Leu Pro Ala Leu Glu Pro Leu Gly Pro Ser Cys Tyr Gln
        260                 265                 270

Leu Cys Trp Ala Thr Ala Pro Glu Arg Cys Leu Ser Asp Thr Pro Pro
            275                 280                 285

Lys Ala Cys Leu Lys Pro Cys Trp Gly His Leu Pro Pro Gln Pro Asn
        290                 295                 300

Ser Leu Asp Ser Gly Leu Leu Cys Leu Pro Cys Pro Ser Ser His Cys
305                 310                 315                 320

Pro Leu Ala Ser Leu Ser Gly Ser Gln Ala Leu Leu Trp Pro Gly Cys
            325                 330                 335

Pro Leu Leu Tyr Gly Leu Glu
            340

<210> SEQ ID NO 36
<211> LENGTH: 273
<212> TYPE: PRT
<213> ORGANISM: Homo sapiens

<400> SEQUENCE: 36

Met Ser Leu Thr Asn Thr Lys Thr Gly Phe Ser Val Lys Asp Ile Leu
1               5                   10                  15

Asp Leu Pro Asp Thr Asn Asp Glu Glu Gly Ser Val Ala Glu Gly Pro
            20                  25                  30

Glu Glu Glu Asn Glu Gly Pro Glu Pro Ala Lys Arg Ala Gly Pro Leu
        35                  40                  45

Gly Gln Gly Ala Leu Asp Ala Val Gln Ser Leu Pro Leu Lys Asn Pro
    50                  55                  60

Phe Tyr Asp Ser Ser Asp Asn Pro Tyr Thr Arg Trp Leu Ala Ser Thr
65                  70                  75                  80

Glu Gly Leu Gln Tyr Ser Leu His Gly Leu Ala Ala Gly Ala Pro Pro
            85                  90                  95

Gln Asp Ser Ser Ser Lys Ser Pro Glu Pro Ser Ala Asp Glu Ser Pro
        100                 105                 110

Asp Asn Asp Lys Glu Thr Pro Gly Gly Gly Asp Ala Gly Lys Lys
        115                 120                 125

Arg Lys Arg Arg Val Leu Phe Ser Lys Ala Gln Thr Tyr Glu Leu Glu
    130                 135                 140

Arg Arg Phe Arg Gln Gln Arg Tyr Leu Ser Ala Pro Glu Arg Glu His
145                 150                 155                 160

Leu Ala Ser Leu Ile Arg Leu Thr Pro Thr Gln Val Lys Ile Trp Phe
            165                 170                 175

Gln Asn His Arg Tyr Lys Met Lys Arg Ala Arg Ala Glu Lys Gly Met
        180                 185                 190
```

```
Glu Val Thr Pro Leu Pro Ser Pro Arg Arg Val Ala Pro Val Leu
            195                 200                 205

Val Arg Asp Gly Lys Pro Cys His Ala Leu Lys Ala Gln Asp Leu Ala
210                 215                 220

Ala Ala Thr Phe Gln Ala Gly Ile Pro Phe Ser Ala Tyr Ser Ala Gln
225                 230                 235                 240

Ser Leu Gln His Met Gln Tyr Asn Ala Gln Tyr Ser Ser Ala Ser Thr
                245                 250                 255

Pro Gln Tyr Pro Thr Ala His Pro Leu Val Gln Ala Gln Trp Thr
            260                 265                 270

Trp

<210> SEQ ID NO 37
<211> LENGTH: 367
<212> TYPE: PRT
<213> ORGANISM: Homo sapiens

<400> SEQUENCE: 37

Met Leu Ala Val Gly Ala Met Glu Gly Thr Arg Gln Ser Ala Phe Leu
1               5                   10                  15

Leu Ser Ser Pro Pro Leu Ala Ala Leu His Ser Met Ala Glu Met Lys
            20                  25                  30

Thr Pro Leu Tyr Pro Ala Ala Tyr Pro Pro Leu Pro Ala Gly Pro Pro
        35                  40                  45

Ser Ser Ser Ser Ser Ser Ser Ser Ser Pro Ser Pro Leu
50                  55                  60

Gly Thr His Asn Pro Gly Leu Lys Pro Ala Thr Gly Gly Leu
65                  70                  75              80

Ser Ser Leu Gly Ser Pro Pro Gln Gln Leu Ser Ala Ala Thr Pro His
                85                  90                  95

Gly Ile Asn Asn Ile Leu Ser Arg Pro Ser Met Pro Val Ala Ser Gly
            100                 105                 110

Ala Ala Leu Pro Ser Ala Ser Pro Ser Gly Ser Ser Ser Ser Ser Ser
        115                 120                 125

Ser Ser Ala Ser Ala Ser Ala Ser Ala Ala Ala Ala Ala Ala
    130                 135                 140

Ala Ala Ala Ala Ala Ser Ser Pro Ala Gly Leu Leu Ala Gly Leu
145                 150                 155             160

Pro Arg Phe Ser Ser Leu Ser Pro Pro Pro Pro Gly Leu Tyr
                165                 170                 175

Phe Ser Pro Ser Ala Ala Val Ala Ala Val Gly Arg Tyr Pro Lys
            180                 185                 190

Pro Leu Ala Glu Leu Pro Gly Arg Thr Pro Ile Phe Trp Pro Gly Val
        195                 200                 205

Met Gln Ser Pro Pro Trp Arg Asp Ala Arg Leu Ala Cys Thr Pro His
    210                 215                 220

Gln Gly Ser Ile Leu Leu Asp Lys Asp Gly Lys Arg Lys His Thr Arg
225                 230                 235                 240

Pro Thr Phe Ser Gly Gln Gln Ile Phe Ala Leu Glu Lys Thr Phe Glu
                245                 250                 255

Gln Thr Lys Tyr Leu Ala Gly Pro Glu Arg Ala Arg Leu Ala Tyr Ser
            260                 265                 270

Leu Gly Met Thr Glu Ser Gln Val Lys Val Trp Phe Gln Asn Arg Arg
        275                 280                 285
```

```
Thr Lys Trp Arg Lys Lys His Ala Ala Glu Met Ala Thr Ala Lys Lys
        290                 295                 300

Lys Gln Asp Ser Glu Thr Glu Arg Leu Lys Gly Ala Ser Glu Asn Glu
305                 310                 315                 320

Glu Glu Asp Asp Asp Tyr Asn Lys Pro Leu Asp Pro Asn Ser Asp Asp
                    325                 330                 335

Glu Lys Ile Thr Gln Leu Leu Lys Lys His Lys Ser Ser Ser Gly Gly
            340                 345                 350

Gly Gly Gly Leu Leu Leu His Ala Ser Glu Pro Glu Ser Ser Ser
        355                 360                 365

<210> SEQ ID NO 38
<211> LENGTH: 349
<212> TYPE: PRT
<213> ORGANISM: Homo sapiens

<400> SEQUENCE: 38

Met Gly Asp Met Gly Asp Pro Lys Lys Lys Arg Leu Ile Ser Leu
1               5                   10                  15

Cys Val Gly Cys Gly Asn Gln Ile His Asp Gln Tyr Ile Leu Arg Val
                20                  25                  30

Ser Pro Asp Leu Glu Trp His Ala Ala Cys Leu Lys Cys Ala Glu Cys
            35                  40                  45

Asn Gln Tyr Leu Asp Glu Ser Cys Thr Cys Phe Val Arg Asp Gly Lys
50                  55                  60

Thr Tyr Cys Lys Arg Asp Tyr Ile Arg Leu Tyr Gly Ile Lys Cys Ala
65                  70                  75                  80

Lys Cys Ser Ile Gly Phe Ser Lys Asn Asp Phe Val Met Arg Ala Arg
                85                  90                  95

Ser Lys Val Tyr His Ile Glu Cys Phe Arg Cys Val Ala Cys Ser Arg
            100                 105                 110

Gln Leu Ile Pro Gly Asp Glu Phe Ala Leu Arg Glu Asp Gly Leu Phe
        115                 120                 125

Cys Arg Ala Asp His Asp Val Val Glu Arg Ala Ser Leu Gly Ala Gly
130                 135                 140

Asp Pro Leu Ser Pro Leu His Pro Ala Arg Pro Leu Gln Met Ala Ala
145                 150                 155                 160

Glu Pro Ile Ser Ala Arg Gln Pro Ala Leu Arg Pro His Val His Lys
                165                 170                 175

Gln Pro Glu Lys Thr Thr Arg Val Arg Thr Val Leu Asn Glu Lys Gln
            180                 185                 190

Leu His Thr Leu Arg Thr Cys Tyr Ala Ala Asn Pro Arg Pro Asp Ala
        195                 200                 205

Leu Met Lys Glu Gln Leu Val Glu Met Thr Gly Leu Ser Pro Arg Val
210                 215                 220

Ile Arg Val Trp Phe Gln Asn Lys Arg Cys Lys Asp Lys Lys Arg Ser
225                 230                 235                 240

Ile Met Met Lys Gln Leu Gln Gln Gln Pro Asn Asp Lys Thr Asn
                245                 250                 255

Ile Gln Gly Met Thr Gly Thr Pro Met Val Ala Ala Ser Pro Glu Arg
            260                 265                 270

His Asp Gly Gly Leu Gln Ala Asn Pro Val Glu Val Gln Ser Tyr Gln
        275                 280                 285

Pro Pro Trp Lys Val Leu Ser Asp Phe Ala Leu Gln Ser Asp Ile Asp
290                 295                 300
```

```
Gln Pro Ala Phe Gln Gln Leu Val Asn Phe Ser Glu Gly Gly Pro Gly
305                 310                 315                 320

Ser Asn Ser Thr Gly Ser Glu Val Ala Ser Met Ser Ser Gln Leu Pro
            325                 330                 335

Asp Thr Pro Asn Ser Met Val Ala Ser Pro Ile Glu Ala
        340                 345

<210> SEQ ID NO 39
<211> LENGTH: 283
<212> TYPE: PRT
<213> ORGANISM: Homo sapiens

<400> SEQUENCE: 39

Met Asn Gly Glu Glu Gln Tyr Tyr Ala Ala Thr Gln Leu Tyr Lys Asp
1               5                   10                  15

Pro Cys Ala Phe Gln Arg Gly Pro Ala Pro Glu Phe Ser Ala Ser Pro
            20                  25                  30

Pro Ala Cys Leu Tyr Met Gly Arg Gln Pro Pro Pro Pro Pro Pro His
        35                  40                  45

Pro Phe Pro Gly Ala Leu Gly Ala Leu Glu Gln Gly Ser Pro Pro Asp
    50                  55                  60

Ile Ser Pro Tyr Glu Val Pro Pro Leu Ala Asp Asp Pro Ala Val Ala
65                  70                  75                  80

His Leu His His His Leu Pro Ala Gln Leu Ala Leu Pro His Pro Pro
                85                  90                  95

Ala Gly Pro Phe Pro Glu Gly Ala Glu Pro Gly Val Leu Glu Glu Pro
            100                 105                 110

Asn Arg Val Gln Leu Pro Phe Pro Trp Met Lys Ser Thr Lys Ala His
        115                 120                 125

Ala Trp Lys Gly Gln Trp Ala Gly Gly Ala Tyr Ala Ala Glu Pro Glu
    130                 135                 140

Glu Asn Lys Arg Thr Arg Thr Ala Tyr Thr Arg Ala Gln Leu Leu Glu
145                 150                 155                 160

Leu Glu Lys Glu Phe Leu Phe Asn Lys Tyr Ile Ser Arg Pro Arg Arg
                165                 170                 175

Val Glu Leu Ala Val Met Leu Asn Leu Thr Glu Arg His Ile Lys Ile
            180                 185                 190

Trp Phe Gln Asn Arg Arg Met Lys Trp Lys Lys Glu Glu Asp Lys Lys
        195                 200                 205

Arg Gly Gly Gly Thr Ala Val Gly Gly Gly Val Ala Glu Pro Glu
    210                 215                 220

Gln Asp Cys Ala Val Thr Ser Gly Glu Glu Leu Leu Ala Leu Pro Pro
225                 230                 235                 240

Pro Pro Pro Pro Gly Gly Ala Val Pro Ala Ala Pro Val Ala Ala
                245                 250                 255

Arg Glu Gly Arg Leu Pro Pro Gly Leu Ser Ala Ser Pro Gln Pro Ser
            260                 265                 270

Ser Val Ala Pro Arg Arg Pro Gln Glu Pro Arg
        275                 280

<210> SEQ ID NO 40
<211> LENGTH: 214
<212> TYPE: PRT
<213> ORGANISM: Homo sapiens
```

```
<400> SEQUENCE: 40

Met Thr Pro Gln Pro Ser Gly Ala Pro Thr Val Gln Val Thr Arg Glu
1               5                   10                  15

Thr Glu Arg Ser Phe Pro Arg Ala Ser Glu Asp Glu Val Thr Cys Pro
            20                  25                  30

Thr Ser Ala Pro Pro Ser Pro Thr Arg Thr Arg Gly Asn Cys Ala Glu
        35                  40                  45

Ala Glu Glu Gly Gly Cys Arg Gly Ala Pro Arg Lys Leu Arg Ala Arg
    50                  55                  60

Arg Gly Gly Arg Ser Arg Pro Lys Ser Glu Leu Ala Leu Ser Lys Gln
65                  70                  75                  80

Arg Arg Ser Arg Arg Lys Lys Ala Asn Asp Arg Glu Arg Asn Arg Met
                85                  90                  95

His Asn Leu Asn Ser Ala Leu Asp Ala Leu Arg Gly Val Leu Pro Thr
            100                 105                 110

Phe Pro Asp Asp Ala Lys Leu Thr Lys Ile Glu Thr Leu Arg Phe Ala
            115                 120                 125

His Asn Tyr Ile Trp Ala Leu Thr Gln Thr Leu Arg Ile Ala Asp His
            130                 135                 140

Ser Leu Tyr Ala Leu Glu Pro Pro Ala Pro His Cys Gly Glu Leu Gly
145                 150                 155                 160

Ser Pro Gly Gly Ser Pro Gly Asp Trp Gly Ser Leu Tyr Ser Pro Val
                165                 170                 175

Ser Gln Ala Gly Ser Leu Ser Pro Ala Ala Ser Leu Glu Glu Arg Pro
                180                 185                 190

Gly Leu Leu Gly Ala Thr Ser Ser Ala Cys Leu Ser Pro Gly Ser Leu
            195                 200                 205

Ala Phe Ser Asp Phe Leu
            210
```

US 8,927,274 B2

POPULATIONS OF PANCREATIC PROGENITOR CELLS AND METHODS OF ISOLATING AND USING SAME

RELATED APPLICATIONS

This application is a National Phase of PCT Patent application No. PCT/IL2011/000302 having International filing date of Apr. 12, 2011, which claims the benefit of priority under 35 USC §119(e) of U.S. Provisional Patent Application No. 61/322,942 filed on Apr. 12, 2010. The contents of the above applications are all incorporated by reference as if fully set forth herein in their entirety.

FIELD AND BACKGROUND OF THE INVENTION

The present invention, in some embodiments thereof, relates to populations of pancreatic progenitor cells and methods of isolating and using same.

The incidence of both Type 1 (T1DM) and Type 2 (T2DM) diabetes is increasing worldwide. β-cell loss and subsequent hyperglycemia associated with Type 1 diabetes result in debilitating short and long term complications (such as retinopathy, neuropathy and nephropathy).

The conventional treatment for diabetes is Insulin administration. However, this does not prevent the long-term complications of the disease, since the optimal insulin dosage is difficult to adjust. Another treatment for diabetes is the transplantation of insulin producing cells. A possible source of such cells is terminally differentiated, postmitotic islet cells. However, these are difficult to expand in tissue culture. Adult and fetal human islet cells grown on HTB-9 matrix in RPMI 1640 medium containing 11 mM glucose, and supplemented with 10% FBS and hepatocyte growth factor, were shown to proliferate at the most for 10-15 population doublings, after which they underwent senescence. The replication span could not be extended by expression of the catalytic subunit of human telomerase (hTERT), which was introduced into the cells with a retrovirus (Halvorsen T L, Beattie G M, Lopez A D, Hayek A, Levine F. J Endocrinol 2000; 166:103-109). Due to massive cell death, this method resulted in a 3-4 expansion of the islet cell mass. The scarcity of cadaveric donors to treat diabetic patients emphasizes the need to search for alternative sources to obtain insulin producing cells.

An alternative to forced expansion of post-mitotic β cells is the induction of differentiation of stem/progenitor cells, which have a natural self-expansion capacity, into insulin-producing cells. Various groups have suggested different differentiation protocols based on the normal differentiation pathways that operate during intra-uterine development (see for example D'Amour, Nature Biotechnology 2006; Jiang, Stem cells, 2007; and Kroon Nature Biotechnology 2008). However, directed differentiation of embryonic stem cells has generated cells that only produce low amounts of insulin, compared to β cells.

The earliest human pancreatic progenitors are marked by the transcription factors pancreatic duodenal homeobox 1(PDX1) and SOX9 (Piper et al, Diabetlogia 2002, 45(7) 1045-7; J. Endocrinol 2004, 181(10 11-23). PDX1 is the first molecular marker identified in the gut region when the foregut endoderm becomes committed to the pancreatic lineage. It is initially detected at day 8.5 of the mouse embryo in the part of the dorsal and ventral primitive gut epithelium that later develops into the pancreas. A high expression is maintained in most epithelial cells of the pancreatic bud until embryonic day 10.5 and then decreases and reappears in the differentiated β-cell. In mature β-cells, PDX-1 transactivates the insulin gene and other genes involved in glucose sensing and metabolism, such as GLUT2 and glucokinase (Watada H 1996, Ahlgren U 1998). Heterozygous mutations in the PDX1 result in impaired glucose tolerance and symptoms of diabetes as seen in MODY4 and late-onset Type II (non-insulin-dependent) diabetes mellitus.

In the mammalian blastocyst, glucose is the most important energy substrate. Its uptake is mediated by glucose transporters (GLUT). The glucose transporter family is composed of at least 12 members, each having twelve membrane-spanning regions with intracellular located amino- and carboxyl-termini. The facilitative transporters (GLUT) utilize the diffusion gradient of glucose (and other sugars) across plasma membranes and exhibit different substrate specificities, kinetic properties and tissue expression profiles. At least six GLUT isoforms are expressed in mammalian embryos (Santos 2006, Hogan 1991, Aghayan 1992). While GLUT1 was found in all the pre-implantation stages, GLUT2 and 3 were detected only in eight-cell embryos, and GLUT4 and 8 at the blastocyst stage. The GLUT2 gene is expressed in the liver, the small intestine, the kidney, some restricted areas of the brain, and in insulin-secreting β-cells of endocrine pancreas. GLUT2 also plays an important role in the adult pancreas and liver. In the β-cells, GLUT2 contributes to the glucose-sensing mechanism, while in the liver it is expressed on the sinusoidal membrane of hepatocytes and allows the bi-directional transport of glucose under hormonal control. The ability of beta cells to release insulin in response to changes in glucose concentration is dependent, in part, on the presence of GLUT2 transporters in the cell membrane. GLUT2 transporters are therefore used as a marker for beta cell maturity. Tonack S et al (Differentiation 2006 74(9-10) 499-509) characterized the glucose transporters in mouse embryonic stem cells, finding that both spontaneously differentiated EBs and mouse blastocysts regulate their glucose input in a similar way.

SUMMARY OF THE INVENTION

According to an aspect of some embodiments of the present invention there is provided a method of generating pancreatic progenitor cells the method comprising:

(a) differentiating stem cells under conditions such that at least a portion of the cells express glucose transporter 2 (GLUT2) so as to generate GLUT2-expressing cells; and (b) enriching for the GLUT2-expressing cells so as to generate a population of GLUT2 enriched cells, wherein at least 80% of the population of GLUT2 enriched cells express GLUT2, thereby generating pancreatic progenitor cells.

According to an aspect of some embodiments of the present invention there is provided an isolated population of pancreatic progenitor cells generated according to the method comprising:

(a) differentiating stem cells under conditions such that at least a portion of the cells express glucose transporter 2 (GLUT2) so as to generate GLUT2-expressing cells; and (b) enriching for the GLUT2-expressing cells so as to generate a population of GLUT2 enriched cells, wherein at least 80% of the population of GLUT2 enriched cells express GLUT2.

According to an aspect of some embodiments of the present invention there is provided a pharmaceutical composition comprising the isolated population of pancreatic progenitor cells generated according to the method comprising:

(a) differentiating stem cells under conditions such that at least a portion of the cells express glucose transporter 2 (GLUT2) so as to generate GLUT2-expressing cells; and (b) enriching for the GLUT2-expressing cells so as to generate a population of GLUT2 enriched cells, wherein at least 80% of the population of GLUT2 enriched cells express GLUT2.

According to an aspect of some embodiments of the present invention there is provided a method of generating insulin-producing cells, the method comprising:

(a) differentiating stem cells under conditions such that at least a portion of the cells express GLUT2 so as to generate GLUT2-expressing cells;

(b) enriching for the GLUT2-expressing cells so as to generate a population of GLUT2 enriched cells, wherein at least 80% of the population of GLUT2 enriched cells express GLUT2; and (c) differentiating the population of GLUT2 enriched cells into insulin-producing cells.

According to an aspect of some embodiments of the present invention there is provided an isolated population of insulin producing cells generated according to the method comprising:

(a) differentiating stem cells under conditions such that at least a portion of the cells express GLUT2 so as to generate GLUT2-expressing cells;

(b) enriching for the GLUT2-expressing cells so as to generate a population of GLUT2 enriched cells, wherein at least 80% of the population of GLUT2 enriched cells express GLUT2; and (c) differentiating the population of GLUT2 enriched cells into insulin-producing cells.

According to an aspect of some embodiments of the present invention there is provided a pharmaceutical composition comprising the isolated population of pancreatic progenitor cells generated according to the method comprising:

(a) differentiating stem cells under conditions such that at least a portion of the cells express GLUT2 so as to generate GLUT2-expressing cells;

(b) enriching for the GLUT2-expressing cells so as to generate a population of GLUT2 enriched cells, wherein at least 80% of the population of GLUT2 enriched cells express GLUT2; and (c) differentiating the population of GLUT2 enriched cells into insulin-producing cells.

According to an aspect of some embodiments of the present invention there is provided method of treating Diabetes in a subject in need thereof, the method comprising transplanting a therapeutically effective amount of an isolated population of pancreatic progenitor cells into the subject, wherein the isolated population of pancreatic progenitor cells are generated according to the method comprising:

(a) differentiating stem cells under conditions such that at least a portion of the cells express glucose transporter 2 (GLUT2) so as to generate GLUT2-expressing cells; and (b) enriching for the GLUT2-expressing cells so as to generate a population of GLUT2 enriched cells, wherein at least 80% of the population of GLUT2 enriched cells express GLUT2, thereby generating pancreatic progenitor cells, thereby treating the Diabetes.

According to an aspect of some embodiments of the present invention there is provided a method of treating Diabetes in a subject in need thereof, the method comprising transplanting a therapeutically effective amount of the isolated population of pancreatic progenitor cells into the subject, thereby treating the Diabetes, wherein the isolated population of pancreatic progenitor cells are generated by:

(a) differentiating stem cells under conditions such that at least a portion of the cells express GLUT2 so as to generate GLUT2-expressing cells;

(b) enriching for the GLUT2-expressing cells so as to generate a population of GLUT2 enriched cells, wherein at least 80% of the population of GLUT2 enriched cells express GLUT2; and (c) differentiating the population of GLUT2 enriched cells into insulin-producing cells.

According to some embodiments of the invention, the enriching is effected by detecting surface marker expression of GLUT2.

According to some embodiments of the invention, the stem cells comprise embryonic stem cells.

According to some embodiments of the invention, the stem cells comprise induced pluripotent stem cells.

According to some embodiments of the invention, the stem cells comprise human pluripotent stem cells.

According to some embodiments of the invention, the differentiating stem cells are effected by generating embryoid bodies.

According to some embodiments of the invention, the enriching is effected by detecting surface marker expression of GLUT2.

According to some embodiments of the invention, the stem cells comprise embryonic stem cells.

According to some embodiments of the invention, the stem cells comprise induced pluripotent stem cells.

According to some embodiments of the invention, the stem cells comprise human pluripotent stem cells.

According to some embodiments of the invention, the differentiating stem cells are effected by generating embryoid bodies.

According to some embodiments of the invention, the isolated population of pancreatic progenitor cells is non-genetically modified.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1A is a bar graph illustrating GLUT1-4 expression in H9.2 and 13 developing EBS-Day 0 to 30.

FIG. 1B is a bar graph illustrating GLUT2 expression in H9.2 and 13 developing EBS-Day 0 to 30

FIG. 1C is a bar graph illustrating PDX-1 expression in H9.2 and 13 developing EBS-Day 0 to 30.

FIG. 1D is a photograph of a Western blot analysis of GLUT1-4 in undifferentiated human embryonic stem cells and in 30 day old EBs.

FIG. 1E: Rates of $^3$H-2-deoxyglucose uptake measured in undifferentiated human embryonic stem cells and in 10 day old EBs. The cells were serum-starved for 2 hours, then incubated for 30 minutes in either control medium (blue bars), or with 10 nM insulin (red bars). Within each experiment, data were normalized per cell number, and the results were expressed as a percentage of the basal uptake. Data are presented as mean±SEM of three separate experiments.

FIGS. 2A-C are graphs and photographs illustrating GLUT expression in cells grown in high vs. low glucose concentration.

2A-B. Real time analysis for GLUT2 (A) and PDX1 (B) expression in differentiating EBs grown in high glucose (25 mM) vs. low glucose (5 mM) concentration. Results are presented as expression relative to cells grown in high glucose concentration.

2C Immunofluorescence for GLUT1-3 in EBs Grown in either high or low glucose concentration. GLUT staining (red) and TO-PRO-3 nuclearic staining (blue) are shown in 7 and 14 day old EBs grown in either high glucose (two upper rows), or low glucose concentration (two lower rows). The slides were visualized using confocal microscopy.

FIGS. 3A-D are photographs illustrating confocal microscopy of 14 day old EBs for GLUT2 and PDX1, shown to co-express membranal and cytoplasmic GLUT2 (green) and nuclearic PDX1 (red). Nuclei were stained for TO-PRO-3 (blue). The slides were visualized by confocal microscopy.

FIGS. 4A-C are graphs illustrating expression of markers in fourteen day old 13 embryoid body GLUT2-FACS sorted cells.

FIGS. 4A-B: Fourteen day old EBs were sorted by FACS according to their GLUT2 cellular expression, and RNA was extracted from the GLUT2$^+$ and GLUT2$^-$ populations. RT-qPCR was performed to compare the expression of various markers in the two cell populations. As can be seen, GLUT2 and PDX1 were enriched in the GLUT2$^+$ population (C) as were other markers of the pancreatic lineage (D). Results are presented as expression relative to unsorted cells.

FIG. 4C: FACS analysis for GLUT2 in 14 day old EBs. Bottom dot plot represents GLUT2 stained population in 14 day old EBs, while the upper plot represents the GLUT2 population in cells stained only for IgG (negative control).

Figures 3A, 3B:
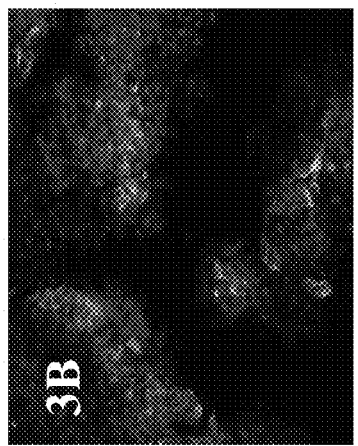
Figures 3C, 3D:
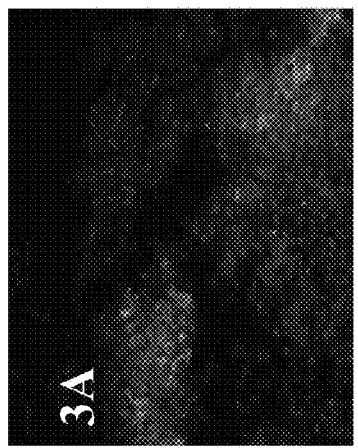
Figure 5B:
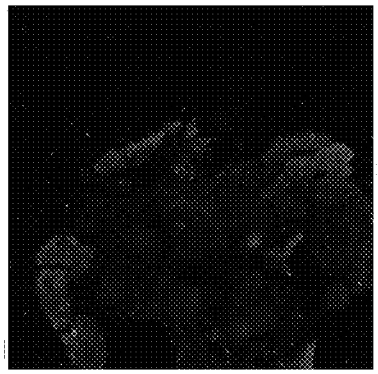
Figure 5C:
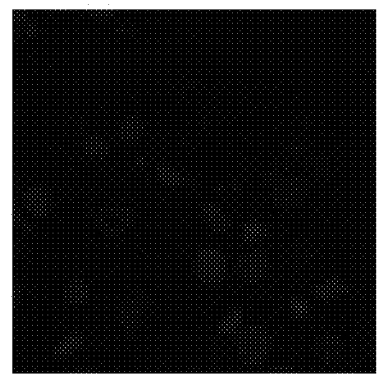
Figure 5A:
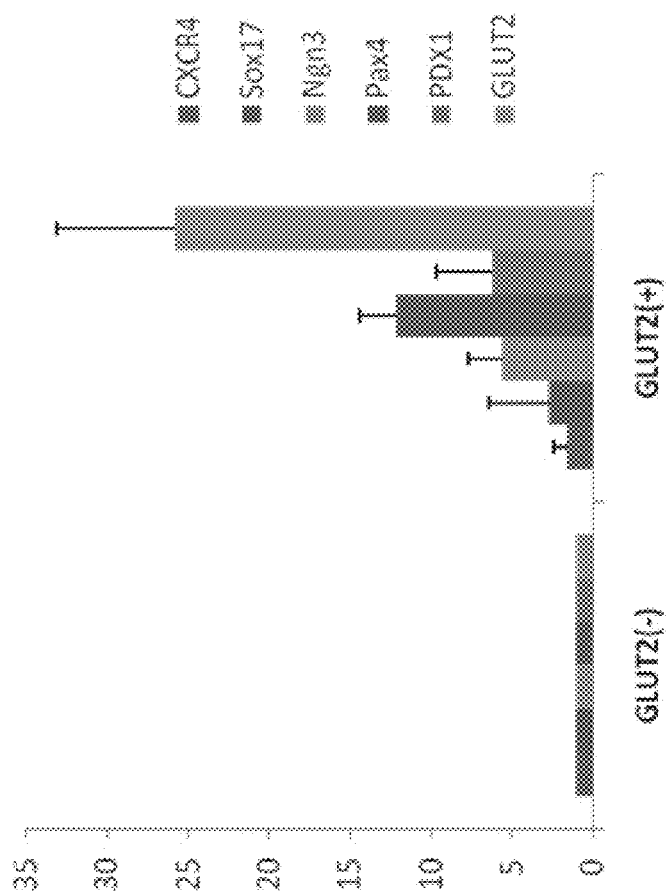

FIGS. 5A-C are graphs and photographs illustrating properties of MACS sorted cells.

FIG. 5A is a bar graph illustrating expression of markers in fourteen day old 13 and H9.2 embryoid body GLUT2-MACS sorted cells.

(−) GLUT2 negative fraction (low expression)

(+) GLUT2 positive fraction (high expression)

FIGS. 5B-C are photographs of immunostaining of MACS-sorted GLUT2 cells. Blue staining reveals the nuclei of the cells. Green staining reveals expression of GLUT2 and red staining reveals expression of PDX-1.

Figure 6:
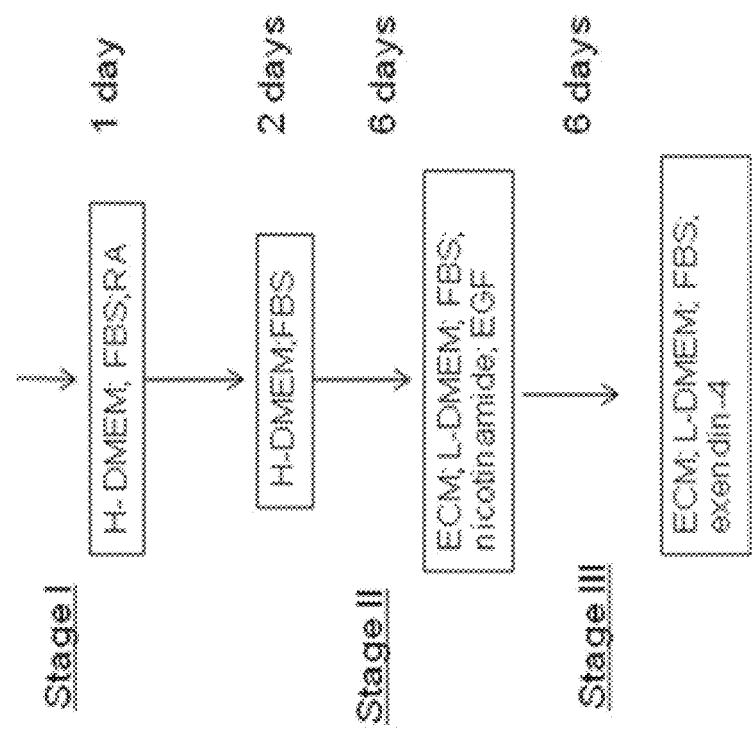

FIG. 6 is a chart describing an exemplary method of differentiating embryonic stem cells towards a pancreatic lineage.

Figure 7:
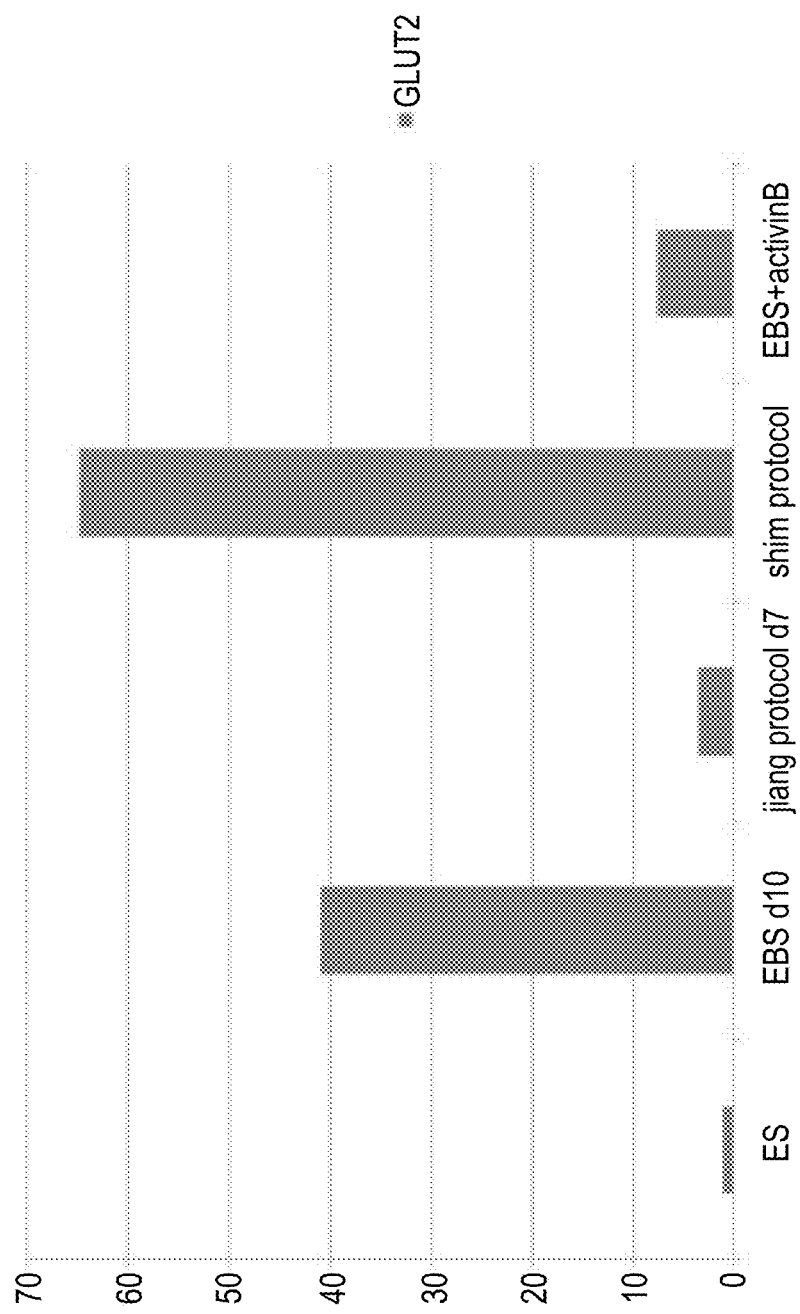

FIG. 7 is a bar graph illustrating the amount of GLUT2 expression in hES cells grown according to different published protocols—ES-undifferentiated cells; EBS D10-EBS grown in medium containing DMEM supplemented with 20% SR; Jiang (Jiang J et al, stem cell 2007); Shim (Shim J H et al, Diabetologia 2007); Addition of Activin B to EBS (Frandsen U et al, BBRC 2007).

Figure 8:
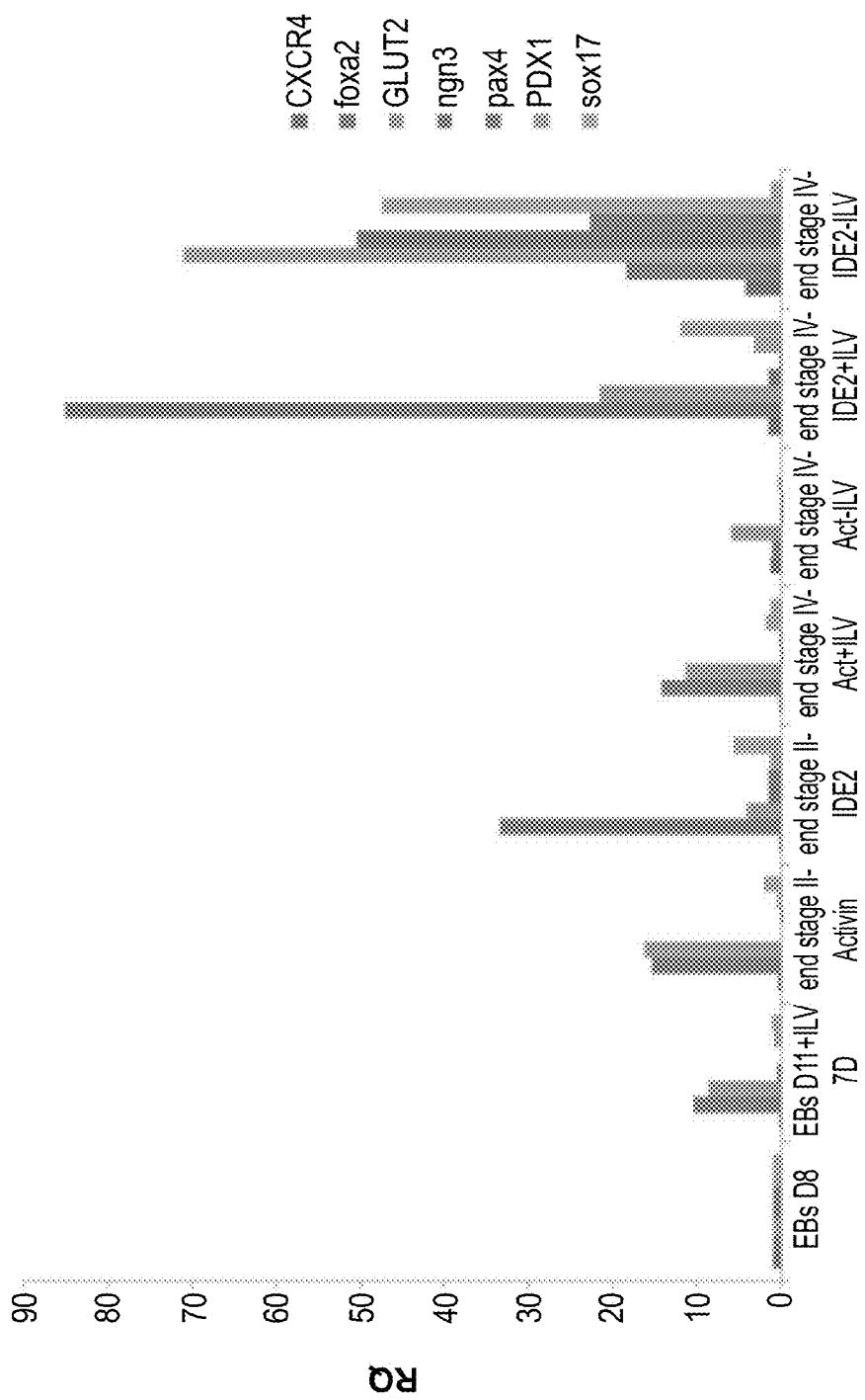

FIG. 8 is a bar graph illustrating the amount of marker expression in hES cells grown according to different published protocols—EBS D8-EBS grown in medium containing DMEM supplemented with 20% SR, addition of Activin A—according to D'Amour 2006, Kroon 2008; addition of IDE2—according to Borouwiak M, cell 2009; addition of ILV—according to Chen S, NCB 2009.

Figure 9:
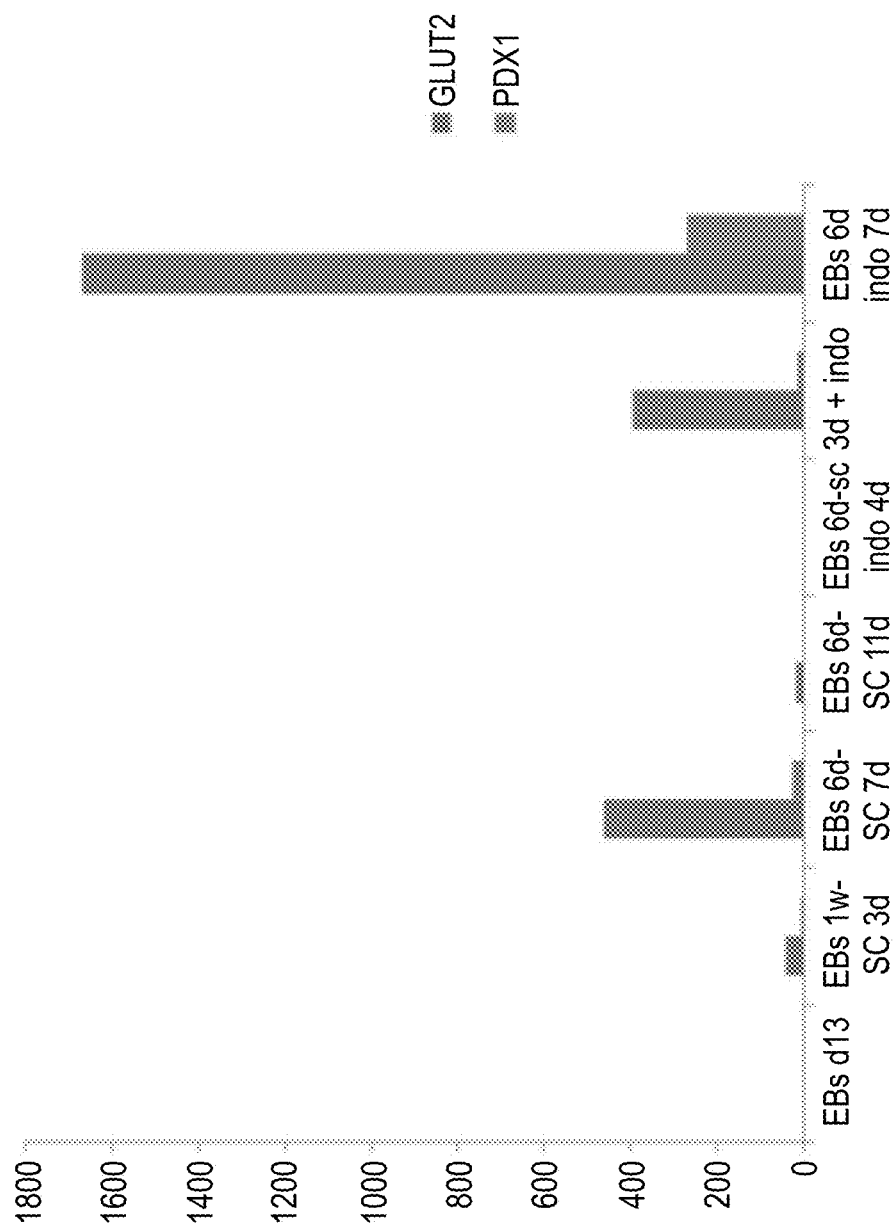

FIG. 9 is a bar graph illustrating the amount of GLUT2 and PDX-1 expression in hES cells grown according to Chen S NCB 2009 5(4) 258-65 and Maehr R et al PNAS 2009, 106 (37)15768-73 (in the presence of indolactam). SC-single cell.

Figure 10:
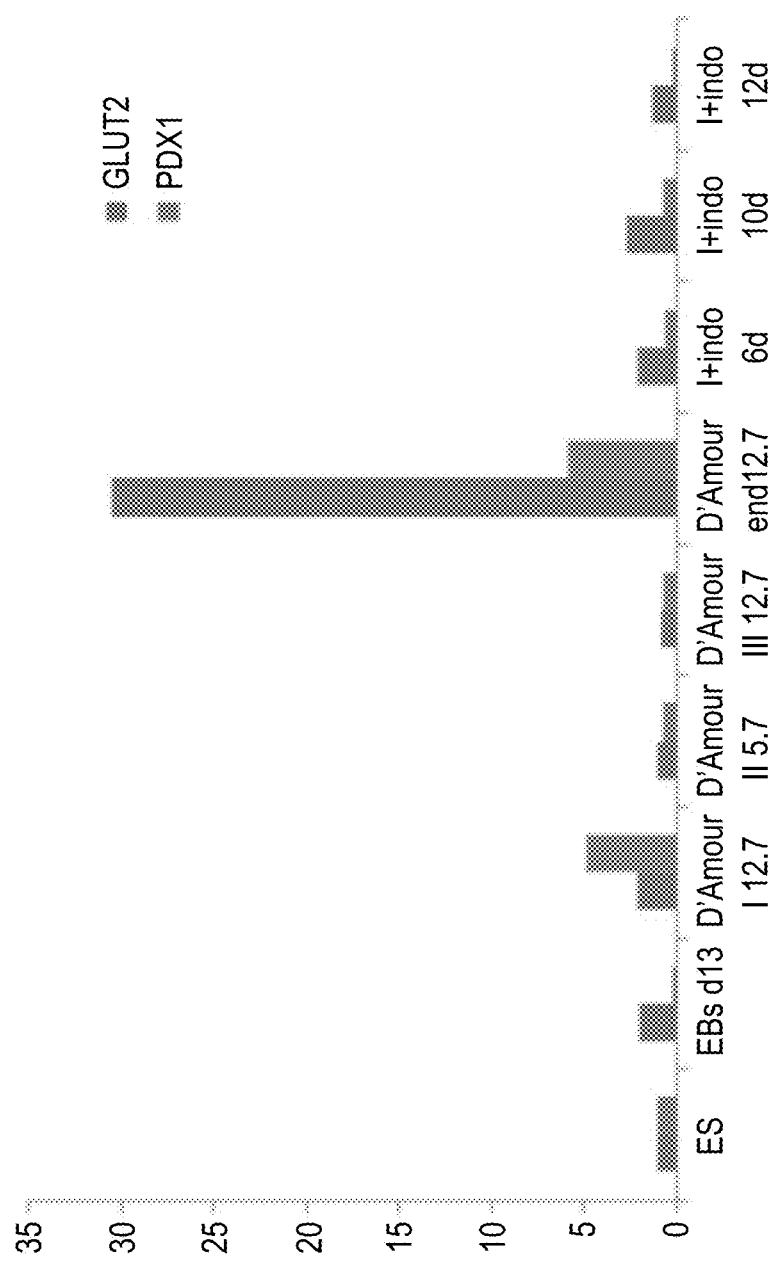

FIG. 10 is a bar graph illustrating the amount of GLUT2 and PDX-1 expression in hES cells grown according to Kroon et al, 2008, Nature Biotechnology 2008 and D'Amour, Nature Biotechnology 2006. I, II and III—refers to stages of the protocol published by Kroon et al.

DESCRIPTION OF SPECIFIC EMBODIMENTS OF THE INVENTION

The present invention, in some embodiments thereof, relates to populations of pancreatic progenitor cells and methods of isolating and using same.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Type I diabetes is caused by the autoimmune destruction of the pancreatic islet insulin-producing beta cells. Insulin administration does not prevent the long-term complications of the disease, since the optimal insulin dosage is difficult to adjust. Replacement of the damaged cells with regulated insulin-producing cells is considered the ultimate cure for type 1 diabetes. Pancreas transplantation has been successful but is severely limited by the shortage of donors.

An alternative to forced expansion of post-mitotic β cells is the induction of differentiation of stem/progenitor cells, (which have a natural self-expansion capacity), into insulin-producing cells. Various groups have suggested different differentiation protocols based on the normal differentiation pathways that operate during intra-uterine development (see for example D'Amour, Nature Biotechnology 2006; Jiang, Stem cells, 2007; and Kroon Nature Biotechnology 2008). However, directed differentiation of embryonic stem cells has generated cells that only produce low amounts of insulin, compared to beta cells.

In an attempt to generate populations of cells that would be effective for treating Diabetes, the present inventors differentiated pluripotent stem cells towards an endodermal lineage and separated them into GLUT2 positive and GLUT2 negative subpopulations. Surprisingly, the present inventors found that there was a correlation between PDX1 and GLUT2 expression in these cells. Specifically, fourteen day old embryoid bodies (EBs) were separated to GLUT2 positive and GLUT2 negative populations, using either FACS ARIA sorter or the MACS kit (magnetic sorting). After sorting, the GLUT2 and PDX1 expression were elevated in the GLUT2 positive cells as well as the expression of other endoderm markers such as PAX4, NGN3, CXCR4 and SOX17 (FIG. 4B and FIG. 5A). Both the positive and negative populations were fixed and stained for the expression of membranal GLUT2 and nuclear PDX1. In the positive population, the majority of the cells co-expressed GLUT2 and PDX1, while those two markers were scarce in the negative population (FIGS. 5B-C).

The present inventors suggest that since sorting of the differentiated cells according to GLUT2 expression significantly increased the percentage of PDX1 expressing cells (and other B cell markers), such cells may be used directly for transplantation or alternatively as a source of cells for further differentiation into insulin-producing cells.

Thus according to an aspect of the present invention, there is provided a method of generating pancreatic progenitor cells the method comprising:

(a) differentiating stem cells under conditions such that at least a portion of the cells express glucose transporter 2 (GLUT2) so as to generate GLUT2-expressing cells; and (b) enriching for the GLUT2-expressing cells so as to generate a population of GLUT2 enriched cells, wherein at least 80% of the population of GLUT2 enriched cells express GLUT2, thereby generating pancreatic progenitor cells.

The phrase "pancreatic progenitor cells" refers to a population of cells which are not fully differentiated into pancreatic cells, yet are committed to differentiating towards at least one type of pancreatic cell—e.g. beta cells that produce insulin; alpha cells that produce glucagon; delta cells (or D cells) that produce somatostatin; and/or F cells that produce pancreatic polypeptide.

Typically, pancreatic progenitor cells express some of the phenotypic markers that are characteristic of pancreatic lineages (e.g. GLUT2, PDX-1 Hnf3β, PC1/3, Beta2, NRx2.2 and PC2). Typically, they do not produce progeny of other embryonic germ layers when cultured by themselves in vitro, unless dedifferentiated or reprogrammed. It will be appreciated that it is not implied that each of the cells within the population have the capacity of forming more than one type of progeny, although individual cells that are multipotent pancreatic progenitor cells may be present.

The method of the present invention is initially effected by obtaining pluripotent stem cells and culturing them.

As used herein, the phrase "stem cells" refers to cells which are capable of remaining in an undifferentiated state (e.g., pluripotent or multipotent stem cells) for extended periods of time in culture until induced to differentiate into other cell types having a particular, specialized function (e.g., fully differentiated cells). Preferably, the phrase "stem cells" encompasses embryonic stem cells (ESCs), induced pluripotent stem cells (iPS), adult stem cells and hematopoietic stem cells. The stem cells are typically mammalian cells, such as for example human stem cells, rodent stem cells (e.g. mouse or rat) or primate stem cells (e.g. monkey).

The phrase "embryonic stem cells" refers to embryonic cells which are capable of differentiating into cells of all three embryonic germ layers (i.e., endoderm, ectoderm and mesoderm), or remaining in an undifferentiated state. The phrase "embryonic stem cells" may comprise cells which are obtained from the embryonic tissue formed after gestation (e.g., blastocyst) before implantation of the embryo (i.e., a pre-implantation blastocyst), extended blastocyst cells (EBCs) which are obtained from a post-implantation/pre-gastrulation stage blastocyst (see WO2006/040763) and embryonic germ (EG) cells which are obtained from the genital tissue of a fetus any time during gestation, preferably before 10 weeks of gestation.

Induced pluripotent stem cells (iPS; embryonic-like stem cells), are cells obtained by de-differentiation of adult somatic cells which are endowed with pluripotency (i.e., being capable of differentiating into the three embryonic germ cell layers, i.e., endoderm, ectoderm and mesoderm). According to some embodiments of the invention, such cells are obtained from a differentiated tissue (e.g., a somatic tissue such as skin) and undergo de-differentiation by genetic manipulation which re-program the cell to acquire embryonic stem cells characteristics. According to some embodiments of the invention, the induced pluripotent stem cells are formed by inducing the expression of Oct-4, Sox2, Kfl4 and c-Myc in a somatic stem cell.

The phrase "adult stem cells" (also called "tissue stem cells" or a stem cell from a somatic tissue) refers to any stem cell derived from a somatic tissue [of either a postnatal or prenatal animal (especially the human)]. The adult stem cell is generally thought to be a multipotent stem cell, capable of differentiation into multiple cell types. Adult stem cells can be derived from any adult, neonatal or fetal tissue such as adipose tissue, skin, kidney, liver, prostate, pancreas, intestine, bone marrow and placenta.

Hematopoietic stem cells, which may also referred to as adult tissue stem cells, include stem cells obtained from blood or bone marrow tissue of an individual at any age or from cord blood of a newborn individual. Preferred stem cells according to this aspect of the present invention are embryonic stem cells, preferably of a human or primate (e.g., monkey) origin.

Placental and cord blood stem cells may also be referred to as "young stem cells".

The embryonic stem cells of the present invention can be obtained using well-known cell-culture methods. For example, human embryonic stem cells can be isolated from human blastocysts. Human blastocysts are typically obtained from human in vivo preimplantation embryos or from in vitro fertilized (IVF) embryos. Alternatively, a single cell human embryo can be expanded to the blastocyst stage. For the isolation of human ES cells the zona pellucida is removed from the blastocyst and the inner cell mass (ICM) is isolated by immunosurgery, in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 4-7 days. For further details on methods of preparation human ES cells see Thomson et al., [U.S. Pat. No. 5,843,780; Science 282: 1145, 1998; Curr. Top. Dev. Biol. 38: 133, 1998; Proc. Natl. Acad. Sci. USA 92: 7844, 1995]; Bongso et al., [Hum Reprod 4: 706, 1989]; and Gardner et al., [Feral. Steril. 69: 84, 1998].

It will be appreciated that commercially available stem cells can also be used with this aspect of the present invention. Human ES cells can be purchased from the NIH human embryonic stem cells registry (wwwdotescrdotnihdotgov). Non-limiting examples of commercially available embryonic stem cell lines are BG01, BG02, BG03, BG04, CY12, CY30, CY92, CY10, TE03 and TE32.

In addition, ES cells can be obtained from other species as well, including mouse (Mills and Bradley, 2001), golden hamster [Doetschman et al., 1988, Dev Biol. 127: 224-7], rat [Iannaccone et al., 1994, Dev Biol. 163: 288-92] rabbit [Giles et al. 1993, Mol Reprod Dev. 36: 130-8; Graves & Moreadith, 1993, Mol Reprod Dev. 1993, 36: 424-33], several domestic animal species [Notarianni et al., 1991, J Reprod Fertil Suppl. 43: 255-60; Wheeler 1994, Reprod Fertil Dev. 6: 563-8; Mitalipova et al., 2001, Cloning. 3: 59-67] and non-human primate species (Rhesus monkey and marmoset) [Thomson et al., 1995, Proc Natl Acad Sci USA. 92: 7844-8; Thomson et al., 1996, Biol Reprod. 55: 254-9].

Extended blastocyst cells (EBCs) can be obtained from a blastocyst of at least nine days post fertilization at a stage prior to gastrulation. Prior to culturing the blastocyst, the zona pellucida is digested [for example by Tyrode's acidic solution (Sigma Aldrich, St Louis, Mo., USA)] so as to expose the inner cell mass. The blastocysts are then cultured as whole embryos for at least nine and no more than fourteen days post fertilization (i.e., prior to the gastrulation event) in vitro using standard embryonic stem cell culturing methods.

EG cells are prepared from the primordial germ cells obtained from fetuses of about 8-11 weeks of gestation (in the case of a human fetus) using laboratory techniques known to anyone skilled in the arts. The genital ridges are dissociated and cut into small chunks which are thereafter disaggregated into cells by mechanical dissociation. The EG cells are then grown in tissue culture flasks with the appropriate medium. The cells are cultured with daily replacement of medium until a cell morphology consistent with EG cells is observed, typically after 7-30 days or 1-4 passages. For additional details on methods of preparation human EG cells see Shamblott et al., [Proc. Natl. Acad. Sci. USA 95: 13726, 1998] and U.S. Pat. No. 6,090,622.

Induced pluripotent stem cells (iPS) (embryonic-like stem cells) can be generated from somatic cells by genetic manipulation of somatic cells, e.g., by retroviral transduction of somatic cells such as fibroblasts, hepatocytes, gastric epithelial cells with transcription factors such as Oct-3/4, Sox2, c-Myc, and KLF4 [Yamanaka S, Cell Stem Cell. 2007, 1(1): 39-49; Aoi T, et al., Generation of Pluripotent Stem Cells from Adult Mouse Liver and Stomach Cells. Science. 2008 Feb. 14. (Epub ahead of print); IH Park, Zhao R, West J A, et al. Reprogramming of human somatic cells to pluripotency with defined factors. Nature 2008; 451:141-146; K Takahashi, Tanabe K, Ohnuki M, et al. Induction of pluripotent stem cells from adult human fibroblasts by defined factors. Cell 2007; 131:861-872]. Other embryonic-like stem cells can be generated by nuclear transfer to oocytes, fusion with embryonic stem cells or nuclear transfer into zygotes if the recipient cells are arrested in mitosis.

It will be appreciated that undifferentiated stem cells are of a distinct morphology, which is clearly distinguishable from differentiated cells of embryo or adult origin by the skilled in the art. Typically, undifferentiated stem cells have high nuclear/cytoplasmic ratios, prominent nucleoli and compact colony formation with poorly discernable cell junctions. Additional features of undifferentiated stem cells are further described hereinunder.

Currently practiced ES culturing methods are mainly based on the use of feeder cell layers which secrete factors needed for stem cell proliferation, while at the same time, inhibit their differentiation. Feeder cell free systems have also been used in ES cell culturing, such systems utilize matrices supplemented with serum, cytokines and growth factors as a replacement for the feeder cell layer.

Feeder-layer Based Cultures

Mouse feeder layers—The most common method for culturing ES cells is based on mouse embryonic fibroblasts (MEF) as a feeder cell layer supplemented with tissue culture medium containing serum or leukemia inhibitor factor (LIF) which supports the proliferation and the pluripotency of the ES cells [Thomson J A, Itskovitz-Eldor J, Shapiro S S, Waknitz M A, Swiergiel J J, Marshall V S, Jones J M. (1998). Embryonic stem cell lines derived from human blastocysts. Science 282: 1145-7; Reubinoff B E, Pera M F, Fong C, Trounson A, Bongso A. (2000). Embryonic stem cell lines from human blastocysts: somatic differentiation in vitro. Nat. Biotechnol. 18: 399-404]. MEF cells are derived from day 12-13 mouse embryos in medium supplemented with fetal bovine serum. Under these conditions mouse ES cells can be maintained in culture as pluripotent stem cells, preserving their phenotypical and functional characteristics. However, unlike mouse ES cells, the presence of exogenously added LIF does not prevent differentiation of human ES cells. Furthermore, the use of feeder cells substantially increases the cost of production, and makes scale-up of human ES cell culture impractical. Additionally, the feeder cells are metabolically inactivated to keep them from outgrowing the stem cells, hence it is necessary to have fresh feeder cells for each splitting of human ES culture. Since at present, the separation of feeder cell components from embryonic cells prepared in bulk culture cannot be efficiently achieved, feeder cell layer-prepared ES cultures are not suitable for human therapy.

ES cells can also be cultured on MEF under serum-free conditions using serum replacement supplemented with basic fibroblast growth factor (bFGF) [Amit M, Carpenter M K, Inokuma M S, Chiu C P, Harris C P, Waknitz M A, Itskovitz-Eldor J, Thomson J A. (2000). Clonally derived human embryonic stem cell lines maintain pluripotency and proliferative potential for prolonged periods of culture. Dev. Biol. 227: 271-8]. Under these conditions the cloning efficiency of ES cells is 4 times higher than under fetal bovine serum. In addition, following 6 months of culturing under serum replacement the ES cells still maintain their pluripotency as indicated by their ability to form teratomas which contain all three embryonic germ layers. Although this system uses a better-defined culture conditions, the presence of mouse cells in the culture exposes the human culture to pathogens which restricts their use in cell-based therapy.

Human embryonic fibroblasts or adult fallopian epithelial cells as feeder cell layers—Human ES cells can be grown and maintained using human embryonic fibroblasts or adult fallopian epithelial cells. When grown on these human feeder cells the human ES cells exhibit normal karyotypes, present alkaline phosphatase activity, express Oct-4 and other embryonic cell surface markers including SSEA-3, SSEA-4, TRA-1-60, and GCTM-2, form teratomas in vivo, and retain all key morphological characteristics [Richards M, Fong C Y, Chan W K, Wong P C, Bongso A. (2002). Human feeders support prolonged undifferentiated growth of human inner cell masses and embryonic stem cells. Nat. Biotechnol. 20: 933-6]. However, the major disadvantage of using human embryonic fibroblasts or adult fallopian tube epithelial cells as feeder cells is that both of these cell lines have a limited passage capacity of only 8-10 times, thereby limiting the ability of a prolonged ES growth period. For a prolonged culturing period, the ES cells must be grown on human feeder cells originated from several subjects which results in an increased variability in culture conditions.

Foreskin feeder layers—Human ES cells can be cultured on human foreskin feeder layer as disclosed in U.S. patent application Ser. No. 10/368,045. Foreskin derived feeder cell layers consist of a complete animal-free environment suitable for culturing human ES cells. In addition, foreskin cells can be maintained in culture for as long as 42 passages since their derivation, providing the ES cells with a relatively constant environment. Under these conditions the human ES cells were found to be functionally indistinct from cells grown with alternate protocols (e.g., MEF). Following differentiation, ES cells expressed genes associated with all three embryonal germ layers, in vitro, and formed teratomas in vivo, consisting of tissue arising from all three germ layers. In addition, unlike human fallopian epithelial cells or human embryonic fibroblasts, human ES cells cultured on foreskin feeder layers were maintained in culture in a pluripotent and undifferentiated state for at least 87 passages. However, although foreskin cells can be maintained in culture for long periods (i.e., 42 passages), the foreskin culture system is not well-defined due to differences between separate batches. In addition, human feeder layer-based culture systems would still require the simultaneous growth of both feeder layers and hES cells. Therefore, feeder-free culturing systems have been developed.

Feeder-free Cultures

Stem cells can be grown on a solid surface such as an extracellular matrix (e.g., Matrigel© or laminin) in the presence of a culture medium. Unlike feeder-based cultures which require the simultaneous growth of feeder cells and stem cells and which may result in mixed cell populations, stem cells grown on feeder-free systems are easily separated from the surface. The culture medium used for growing the stem cells contains factors that effectively inhibit differentiation and promote their growth such as MEF-conditioned medium and bFGF. However, commonly used feeder-free culturing systems utilize an animal-based matrix (e.g., Matrigel®) supplemented with mouse or bovine serum, or with MEF conditioned medium [Xu C, et al. (2001). Feeder-free growth of undifferentiated human embryonic stem cells. Nat. Biotechnol. 19: 971-4] which present the risk of animal pathogen cross-transfer to the human ES cells, thus compromising future clinical applications.

Adult tissue stem cells can be isolated using various methods known in the art such as those disclosed by Alison, M. R. [J. Pathol. 2003 200(5): 547-50], Cai, J. et al., [Blood Cells Mol. Dis. 2003 31(1): 18-27], Collins, A. T. et al., [J Cell Sci. 2001; 114(Pt 21): 3865-72], Potten, C. S, and Morris, R. J. [Epithelial stem cells in vivo. 1988. J. Cell Sci. Suppl. 10, 45-62], Dominici, M et al., [J. Biol. Regul. Homeost. Agents. 2001, 15: 28-37], Caplan and Haynesworth [U.S. Pat. No. 5,486,359] Jones E. A. et al., [Arthritis Rheum. 2002, 46(12): 3349-60]. Fetal stem cells can be isolated using various methods to known in the art such as those disclosed by Eventov-Friedman S, et al., PLoS Med. 2006, 3: e215; Eventov-Friedman S, et al., Proc Natl Acad Sci USA. 2005, 102: 2928-33; Dekel B, et al., 2003, Nat. Med. 9: 53-60; and Dekel B, et al., 2002, J. Am. Soc. Nephrol. 13: 977-90. Hematopoietic stem cells can be isolated using various methods known in the arts such as those disclosed by "Handbook of Stem Cells" edit by Robert Lanze, Elsevier Academic Press, 2004, Chapter 54, pp 609-614, isolation and characterization of hematopoietic stem cells, by Gerald J Spangrude and William B Stayton.

Generally, isolation of adult tissue stem cells is based on the discrete location (or niche) of each cell type included in the adult tissue, i.e., the stem cells, the transit amplifying cells and the terminally differentiated cells [Potten, C. S, and Morris, R. J. (1988). Epithelial stem cells in vivo. J. Cell Sci. Suppl. 10, 45-62]. Thus, an adult tissue such as, for example, prostate tissue is digested with Collagenase and subjected to repeated unit gravity centrifugation to separate the epithelial structures of the prostate (e.g., organoids, acini and ducts) from the stromal cells. Organoids are then disaggregated into single cell suspensions by incubation with Trypsin/EDTA (Life Technologies, Paisley, UK) and the basal, CD44-positive, stem cells are isolated from the luminal, CD57-positive, terminally differentiated secretory cells, using anti-human CD44 antibody (clone G44-26; Pharmingen, Becton Dickinson, Oxford, UK) labeling and incubation with MACS (Miltenyi Biotec Ltd, Surrey, UK) goat anti-mouse IgG microbeads. The cell suspension is then applied to a MACS column and the basal cells are eluted and re-suspended in WAJC 404 complete medium [Robinson, E. J. et al. (1998). Basal cells are progenitors of luminal cells in primary cultures of differentiating human prostatic epithelium Prostate 37, 149-160].

Since basal stem cells can adhere to basement membrane proteins more rapidly than other basal cells [Jones, P. H. et al. (1995). Stem cell patterning and fate in human epidermis. Cell 60, 83-93; Shinohara, T., et al. (1999). β1- and α6-integrin are surface markers on mouse spermatogonial stem cells. Proc. Natl. Acad. Sci. USA 96, 5504-5509] the CD44 positive basal cells are plated onto tissue culture dishes coated with either type I collagen (52 µg/ml), type IV collagen (88 µg/ml) or laminin 1 (100 µg/ml; Biocoat®, Becton Dickinson) previously blocked with 0.3% bovine serum albumin to (fraction V, Sigma-Aldrich, Poole, UK) in Dulbecco's phosphate buffered saline (PBS; Oxoid Ltd, Basingstoke, UK). Following 5 minutes, the tissue culture dishes are washed with PBS and adherent cells, containing the prostate tissue basal stem cells are harvested with trypsin-EDTA.

BM-derived Stem Cell, Mesenchymal Stem Cells

The stem cells utilized by the present invention may also be BM-derived stem cells including hematopoietic, stromal or mesenchymal stem cells (Dominici, M et al., 2001. Bone marrow mesenchymal cells: biological properties and clinical applications. J. Biol. Regul. Homeost. Agents. 15: 28-37). BM-derived stem cells may be obtained from iliac crest, femora, tibiae, spine, rib or other medullar spaces.

Mesenchymal stem cells give rise to one or more mesenchymal tissues (e.g., pancreatic, adipose, osseous, cartilaginous, elastic and fibrous connective tissues, myoblasts) as well as to tissues other than those originating in the embryonic mesoderm (e.g., neural cells) depending upon various influences from bioactive factors such as cytokines. Although such cells can be isolated from embryonic yolk sac, placenta, umbilical cord, fetal and adolescent skin, blood and other tissues, their abundance in the BM far exceeds their abundance in other tissues and as such isolation from BM is presently preferred.

Methods of isolating, purifying and expanding mesenchymal stem cells (MSCs) are known in the arts and include, for example, those disclosed by Caplan and Haynesworth in U.S. Pat. No. 5,486,359 and Jones E. A. et al., 2002, Isolation and characterization of bone marrow multipotential mesenchymal progenitor cells, Arthritis Rheum. 46(12): 3349-60.

Preferably, mesenchymal stem cell cultures are generated by diluting BM aspirates (usually 20 ml) with equal volumes of Hank's balanced salt solution (HBSS; GIBCO Laboratories, Grand Island, N.Y., USA) and layering the diluted cells over about 10 ml of a Ficoll column (Ficoll-Paque; Pharmacia, Piscataway, N.J., USA). Following 30 minutes of centrifugation at 2,500×g, the mononuclear cell layer is removed from the interface and suspended in HBSS. Cells are then centrifuged at 1,500×g for 15 minutes and resuspended in a complete medium (MEM, a medium without deoxyribonucleotides or ribonucleotides; GIBCO); 20% fetal calf serum (FCS) derived from a lot selected for rapid growth of MSCs (Atlanta Biologicals, Norcross, Ga.); 100 units/ml penicillin (GIBCO), 100 µg/ml streptomycin (GIBCO); and 2 mM L-glutamine (GIBCO). Resuspended cells are plated in about 25 ml of medium in a 10 cm culture dish (Corning Glass Works, Corning, N.Y.) and incubated at 37° C. with 5% humidified $CO_2$. Following 24 hours in culture, nonadherent cells are discarded, and the adherent cells are thoroughly washed twice with phosphate buffered saline (PBS). The medium is replaced with a fresh complete medium every 3 or 4 days for about 14 days. Adherent cells are then harvested with 0.25% trypsin and 1 mM EDTA (Trypsin/EDTA, GIBCO) for 5 mM at 37° C., replated in a 6-cm plate and cultured for another 14 days. Cells are then trypsinized and counted using a cell counting device such as for example, a hemocytometer (Hausser Scientific, Horsham, Pa.). Cultured cells are recovered by centrifugation and resuspended with 5% DMSO and 30% FCS at a concentration of 1 to $2\times10^6$ cells per ml. Aliquots of about 1 ml each are slowly frozen and stored in liquid nitrogen.

To expand the mesenchymal stem cell fraction, frozen cells are thawed at 37° C., diluted with a complete medium and recovered by centrifugation to remove the DMSO. Cells are resuspended in a complete medium and plated at a concentration of about 5,000 cells/cm$^2$. Following 24 hours in culture, nonadherent cells are removed and the adherent cells are harvested using Trypsin/EDTA, dissociated by passage through a narrowed Pasteur pipette, and preferably replated at a density of about 1.5 to about 3.0 cells/cm$^2$. Under these conditions, MSC cultures can grow for about 50 population doublings and be expanded for about 2000 fold [Colter D C., et al. Rapid expansion of recycling stem cells in cultures of plastic-adherent cells from human bone marrow. Proc Natl Acad Sci USA. 97: 3213-3218, 2000].

As mentioned the stem cells of the present invention are cultured under conditions such that at least a portion thereof express GLUT2.

According to one embodiment the culturing is effected under low glucose concentrations (e.g. less than 15 mM, less than 10 mM or even less than 5 mM).

According to one embodiment, embryonic stem cells (or iPS cells) may be cultured as embryoid bodies for about 14-25 days, or for about 14-21 days, 14-20 days or 14-19 days until GLUT2 is expressed to the required level.

As used herein the phrase "embryoid bodies" (EBs) refers to three dimensional multicellular aggregates of differentiated and undifferentiated cells derivatives of three embryonic germ layers.

Embryoid bodies are formed upon the removal of ES cells (or iPS cells) from feeder layers or feeder cells-free culture systems. ES cells removal can be effected using type IV Collagenase treatment for a limited time. Following dissociation from the culturing surface, the cells are transferred to tissue culture plates containing a culture medium supplemented with serum and amino acids.

During the culturing period, EBs are further monitored for their differentiation state. Cell differentiation can be determined upon examination of cell or tissue-specific markers which are known to be indicative of differentiation. For example, EB-derived-differentiated cells may express the neurofilament 68 KD which is a characteristic marker of the ectoderm cell lineage.

Other protocols are also envisioned by the present invention in order to differentiate the stem cells towards a state such that they express GLUT2. For example the cells may be differentiated using any of the methods described in Example 2 herein below.

Methods useful for monitoring the expression level of GLUT2 are well known in the art and include RT-PCR, semi-quantitative RT-PCR, Northern blot, RNA in situ hybridization, Western blot analysis and immunohistochemistry.

It is expected that during the life of a patent maturing from this application many relevant differentiation protocols will be developed and the scope of the term "differentiated" is intended to include all such new technologies a priori.

Following the culturing step whereby stem cells are differentiated to express GLUT2, the GLUT2-expressing cells are enriched so as to generate a population of cells, wherein at least 50% of the cells express GLUT2, more preferably 60% of the cells express GLUT2, more preferably 70% of the cells express GLUT2, more preferably 80% of the cells express GLUT2, more preferably 90% of the cells express GLUT2, more preferably 100% of the cells express GLUT2.

The enriching may be effected using known cell sorting procedures. It will be appreciated that the enriching may also be effected by depleting of non-relevant subpopulations such as cells expressing CD31 (and endothelial marker).

According to one embodiment, the enriching is effected using a fluorescence-activated cell sorter (FACS).

As used herein, the term "flow cytometry" refers to an assay in which the proportion of a material (e.g. differentiated stem cells expressing GLUT2) in a sample is determined by labeling the material (e.g., by binding a labeled antibody to the material), causing a fluid stream containing the material to pass through a beam of light, separating the light emitted from the sample into constituent wavelengths by a series of filters and mirrors, and detecting the light.

A multitude of flow cytometers are commercially available including for e.g. Becton Dickinson FACScan and FACScalibur (BD Biosciences, Mountain View, Calif.). Antibodies that may be used for FACS analysis are taught in Schlossman S, Boumell L, et al, [Leucocyte Typing V. New York: Oxford University Press; 1995] and are widely commercially available.

The enriching may also be effected by magnetic sorting as described in Example 1 of the Examples section herein below. Essentially, magnetic cell separation may be effected using antibodies and magnetic beads from Dynal. The magnetic beads with attached cells are isolated by insertion of the sample tube in a magnetic rack.

Typically, the mixture of cells to be separated is incubated with magnetic beads coated with antibodies against a particular surface antigen (e.g. GLUT2). This causes the cells expressing this antigen to attach to the magnetic beads. Afterwards the cell solution is transferred on a column placed in a strong magnetic field. In this step, the cells attached to the beads (expressing the antigen) stay on the column, while other cells (not expressing the antigen) flow through. With this method, the cells can be separated positively or negatively with respect to the particular antigen(s).

In positive selection the cells expressing GLUT2, which attached to the magnetic column, are washed out to a separate vessel, after removing the column from the magnetic field. In negative selection the antibody used is against surface antigen(s) which are known to be present on cells that are not of interest, as mentioned herein above. After administration of the cells/magnetic beads solution onto the column the cells expressing these antigens bind to the column and fraction that goes through is collected, as it contains almost no cells with undesired antigens.

Following sorting, isolated cell populations are obtained. The cell populations may be homogeneous (i.e. comprise a single cell type) or heterogeneous (may be made up of a variety of cell types). Thus, the present invention envisages further purification of the cells—e.g. by selecting for additional markers.

As used herein, the term "purified," means that a cell population is essentially free from any other cell type (e.g., feeder fibroblasts).

Cells obtained according to the method of the present invention can be further differentiated towards a desired function. For example, the defined functions of an adult beta cell include storing insulin and secreting insulin in response to glucose. Thus, the GLUT2 expressing stem cells of the present invention may be further differentiated so as to increase beta cell insulin content, increase sensitivity to glucose and/or increase secretory apparatus. Methods of increasing beta cell insulin content may include increasing insulin transcription and/or post transcriptional control and/or increasing translation and/or post-translational control. Methods of increasing beta cell insulin content may also include enhancing insulin storage and/or retarding insulin breakdown. Methods of increasing sensitivity to glucose may include increasing the expression of glucose transporters.

According to one embodiment the GLUT2-expressing stem cells are differentiated using a beta cell differentiation promoting agent.

As used herein a "beta cell differentiation promoting agent" refers to a molecule (e.g., a proteinaceous or nucleic molecule) which is able either alone or in combination with other beta cell differentiation promoting agents to further differentiate the GLUT2-expressing stem cells of the present invention using any of the mechanisms mentioned hereinabove.

Examples of beta cell differentiation promoting agents include but are not limited to Activin A, Atrial Natriuretic Peptide, Betacellulin, Bone Morphogenic Protein (BMP-2), Bone Morphogenic Protein (BMP-4), C natriuretic peptide (CNP), Caerulein, Calcitonin Gene Related Peptide (CGRP-ax), Cholecystokinin (CCK8-amide), Cholecystokinin octapeptide (CCK8-sulfated), Cholera Toxin B Subunit, Corticosterone (Reichstein's substance H), Dexamethasone, DIF-1, Differanisole A, Dimethylsulfoxide (DMSO), EGF, Endothelin 1, Exendin 4, FGF acidic, FGF2, FGF7, FGFb, Gastrin I, Gastrin Releasing Peptide (GRP), Glucagon-Like Peptide 1 (GLP-1), Glucose, Growth Hormone, Hepatocyte Growth Factor (HGF), IGF-1, IGF-2, Insulin, KGF, Lactogen, Laminin, Leu-Enkephalin, Leukemia Inhibitory Factor (LIF), Met-Enkephalin, n Butyric Acid, Nerve Growth Factor (.beta.-NGF), Nicotinamide, n-n-dimethylformamide (DMF), Parathyroid Hormone Related Peptide (Pth II RP), PDGF AA+PDGF BB MIX, PIGF (Placental GF), Progesterone, Prolactin, Putrescine Dihydrochloride Gamma-Irradiated Cell Culture, REG1, Retinoic Acid, Selenium, Selenious Acid, Sonic Hedgehog, Soybean Trypsin Inhibitor, Substance P, Superoxide Dismutase (SOD), TGF-alpha, TGF-beta. sRII, TGF-beta.1, transferrin, Triiodothyronine (T3), Trolox, Vasoactive Intestinal Peptide (VIP), VEGF, Vitamin A and Vitamin E.

A beta cell differentiation promoting agent may also be a transcription factor. The term "beta cell differentiation transcription factor" as used herein is defined as any molecule, either a polypeptide or a nucleic acid expressing the polypeptide, which is involved in beta cell differentiation by functioning as a transcription factor. The transcription factor may also participate in additional mechanisms directed to development, metabolism or the like. Examples of beta cell differentiation transcription factor include, but are not limited to, NeuroD (GenBank Accession No. AAA93480 (SEQ ID NO: 33)), Pax6 (GenBank Accession No. AAK95849(SEQ ID NO: 34)), Pax4 (GenBank Accession No. AAD02289 (SEQ ID NO: 35)), NRx2.2 (GenBank Accession No. AAC83132 (SEQ ID NO: 36)), NRx6.1 (GenBank Accession No. AAD11962 (SEQ ID NO: 37)), Is1-1 (GenBank Accession No. NP002193(SEQ ID NO: 38)), Pd-x (GenBank Accession No. AAA88020 (SEQ ID NO: 39)) or Ngn3 (GenBank Accession No. AAK15022 (SEQ ID NO: 40)) and homologues or orthologues of same.

Polypeptide agents for promoting beta cell differentiation may be provided to the adult islet beta cells per se (i.e. added to the culture medium). Alternatively, polynucleotides encoding same may be administered to the adult islet beta cells. In this case, the polynucleotide agent is ligated in a nucleic acid construct under the control of a cis-acting regulatory element (e.g. promoter) capable of directing an expression of the beta cell differentiation promoting agent in the adult islet beta cells in a constitutive or inducible manner.

The nucleic acid construct may be introduced into the GLUT2 expressing stem cells of the present invention using an appropriate gene delivery vehicle/method (transfection, transduction, etc.) and an appropriate expression system. Examples of suitable constructs include, but are not limited to, pcDNA3, pcDNA3.1 (+/−), pGL3, PzeoSV2 (+/−), pDisplay, pEF/myc/cyto, pCMV/myc/cyto each of which is commercially available from Invitrogen Co. (wwwdotinvitrogendotcom). Lipid-based systems may be used for the delivery of these constructs into the expanded adult islet beta cells of the present invention. Useful lipids for lipid-mediated transfer of the gene are, for example, DOTMA, DOPE, and DC-Chol [Tonkinson et al., Cancer Investigation, 14(1): 54-65 (1996)]. Recently, it has been shown that Chitosan can be used to deliver nucleic acids to the intestine cells (Chen J. (2004) World J Gastroenterol 10(1):112-116). Other non-lipid based vectors that can be used according to this aspect of the present invention include but are not limited to polylysine and dendrimers.

The expression construct may also be a virus. Examples of viral constructs include but are not limited to adenoviral vectors, retroviral vectors, vaccinia viral vectors, adeno-associated viral vectors, polyoma viral vectors, alphaviral vectors, rhabdoviral vectors, lenti viral vectors and herpesviral vectors.

A viral construct such as a retroviral construct includes at least one transcriptional promoter/enhancer or locus-defining element(s), or other elements that control gene expression by other means such as alternate splicing, nuclear RNA export, or post-transcriptional modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably, the signal sequence for this purpose is a mammalian signal sequence or the signal sequence of the peptide variants of the present invention. Optionally, the construct may also include a signal that directs polyadenylation, as well as one or more restriction site and a translation termination sequence. By way of example, such constructs will typically include a 5' LTR, a tRNA binding site, a packaging signal, an origin of second-strand DNA synthesis, and a 3' LTR or a portion thereof.

Preferably the viral dose for infection is at least $10^3$, $10^4$, $10^5$, $10^6$, $10^7$, $10^8$, $10^9$, $10^{10}$, $10^{11}$, $10^{12}$, $10^{13}$, $10^{14}$, $10^{15}$ or higher pfu or viral particles.

It will be appreciated that expression of more than one beta cell differentiation to promoting agent in the expanded cells of the present invention may be desired. Various construct schemes can be utilized to express more than one beta cell differentiation promoting agent from a single nucleic acid construct.

For example, the two recombinant proteins can be co-transcribed as a polycistronic message from a single promoter sequence of the nucleic acid construct.

To enable co-translation of both beta cell differentiation promoting agents from a single polycistronic message, the first and second polynucleotide segments can be transcriptionally fused via a linker sequence including an internal ribosome entry site (IRES) sequence which enables the translation of the polynucleotide segment downstream of the IRES sequence. In this case, a transcribed polycistronic RNA molecule including the coding sequences of both the first and the second growth factors will be translated from both the capped 5' end and the internal IRES sequence of the polycistronic RNA molecule to thereby produce both beta cell differentiation promoting agents.

Alternatively, the first and second polynucleotide segments can be translationally fused via a protease recognition site cleavable by a protease expressed by the cell to be transformed with the nucleic acid construct. In this case, a chimeric polypeptide translated will be cleaved by the cell expressed protease to thereby generate both beta cell differentiation promoting agents.

Still alternatively, the nucleic acid construct of the present invention can include two promoter sequences each being for separately expressing both beta cell differentiation promoting agents. These two promoters which may be identical or distinct can be constitutive, tissue specific or regulatable (e.g. inducible) promoters functional in one or more cell types.

As mentioned, the beta cell differentiation promoting agents, either alone or in combination, may be provided to ex-vivo cultured adult islet beta cells by addition to the incubating medium. According to one embodiment, the beta cell differentiation promoting agents is provided alone in a quantity that is sufficient to increase insulin content in the GLUT-2 expressing stem cells.

The phrase "insulin content" refers to the amount of mature insulin inside a cell. Measurement of insulin content is well known in the art. An exemplary method is extraction of cellular insulin with 3 M acetic acid as described in the Examples section which follows. The amount of mature insulin extracted from the adult islet beta cells may be determined using an ELISA kit commercially available from Mercodia, Uppsala, Sweden.

The GLUT-2 expressing stem cells of the present invention may be further differentiated such that they become glucose responsive—i.e. secrete insulin in response to glucose.

The population of GLUT-2 expressing stem cells of the present invention may be further modified (e.g. genetic modification) to express a pharmaceutical agent such as a therapeutic agent, a telomerase gene, an agent that reduces immune mediated rejection or a marker gene. It is contemplated that therapeutic agents such as antimetabolites (e.g., purine analogs, pyrimidine analogs), enzyme inhibitors and peptidomimetics may be generally useful in the present invention. An example of a gene that may reduce immune mediated rejection is the uteroglobin gene. Uteroglobin is a protein expressed during pregnancy that confers immunologic tolerance and prevents inflammatory reactions. Methods of genetically modifying the GLUT2 expressing stem cells of the present invention are described hereinabove.

Since the GLUT2 expressing stem cells of the present invention (and the cells differentiated there from) have the potential to store and secrete insulin, they may be used for treating a disease which is associated with insulin deficiency such as diabetes.

Thus according to an aspect of the present invention there is provided a method of treating Diabetes in a subject in need thereof, the method comprising transplanting a therapeutically effective amount of the isolated population of pancreatic progenitor cells generated according to the methods described herein into the subject, thereby treating the Diabetes.

As used herein "Diabetes" refers to a disease resulting either from an absolute deficiency of insulin (type 1 diabetes) due to a defect in the biosynthesis or production of insulin, or a relative deficiency of insulin in the presence of insulin resistance (type 2 diabetes), i.e., impaired insulin action, in an organism. The diabetic patient thus has absolute or relative insulin deficiency, and displays, among other symptoms and signs, elevated blood glucose concentration, presence of glucose in the urine and excessive discharge of urine.

The phrase "treating" refers to inhibiting or arresting the development of a disease, disorder or condition and/or causing the reduction, remission, or regression of a disease, disorder or condition in an individual suffering from, or diagnosed with, the disease, disorder or condition. Those of skill in the art will be aware of various methodologies and assays which can be used to assess the development of a disease, disorder or condition, and similarly, various methodologies and assays which can be used to assess the reduction, remission or regression of a disease, disorder or condition.

As used herein, "transplanting" refers to providing the GLUT2 expressing stem cells (or cells differentiated therefrom) of the present invention, using any suitable route. Typically, beta cell therapy is effected by injection using a catheter into the portal vein of the liver, although other methods of administration are envisaged.

It will be appreciated that the GLUT2 expressing stem cells of the present invention can be derived from either autologous sources or from allogeneic sources such as human cadavers or donors. Since non-autologous cells are likely to induce an immune reaction when administered to the body several approaches have been developed to reduce the likelihood of rejection of non-autologous cells. These include either suppressing the recipient immune system or encapsulating the non-autologous cells in immunoisolating, semipermeable membranes before transplantation.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu M Z, et al., Cell encapsulation with alginate and alpha-phenoxycinnamylidene-acetylated poly(allylamine). Biotechnol Bioeng. 2000, 70: 479-83, Chang T M and Prakash S. Procedures for microencapsulation of enzymes, cells and genetically engineered microorganisms. Mol. Biotechnol. 2001, 17: 249-60, and Lu M Z, et al., A novel cell encapsulation method using photosensitive poly(allylamine alpha-cyanocinnamylideneacetate). J. Microencapsul. 2000, 17: 245-51.

For example, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 μm. Such microcapsules can be further encapsulated with additional 2-5 μm ter-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Thechnol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 μm (Canaple L. et al., Improving cell encapsulation through size control. J Biomater Sci Polym Ed. 2002; 13:783-96). Moreover, nanoporous biocapsules with well-controlled pore size as small as 7 nm, tailored surface chemistries and precise microarchitectures were found to successfully immunoisolate microenvironments for cells (Williams D. Small is beautiful: microparticle and nanoparticle technology in medical devices. Med Device Technol. 1999, 10: 6-9; Desai, T. A. Microfabrication technology for pancreatic cell encapsulation. Expert Opin Biol Ther. 2002, 2: 633-46).

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE.sup.R), etanercept, TNF.alpha. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

The GLUT2 expressing stem cells of the present invention (or cells differentiated therefrom) may be transplanted to a human subject per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the adult islet beta cells of the present invention accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer.

Pharmaceutical compositions suitable for use in context of the present invention include compositions wherein the active ingredients are contained in an amount effective to achieve the intended purpose. More specifically, a therapeutically effective amount means an amount of active ingredients (insulin producing cells) effective to prevent, alleviate or ameliorate symptoms of a disorder (e.g., diabetes) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated from animal models (e.g. STZ diabetic mice) to achieve a desired concentration or titer. Such information can be used to more accurately determine useful doses in humans.

Toxicity and therapeutic efficacy of the active ingredients described herein can be determined by standard pharmaceutical procedures in experimental animals. The data obtained from these animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide cell numbers sufficient to induce normoglycemia (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be to accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

The GLUT2 expressing stem cells of the present invention may also be used for screening biologic or pharmacologic agents with B cell differentiating potential. In addition, differentiated GLUT2 expressing stem cells (which secrete insulin) may be used as a source of insulin—i.e. for in vitro production. The insulin may be stored and provided directly to the diabetic patient.

As used herein the term "about" refers to ±10%

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion. Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Selection of GLUT2 Expressing Cells in Embryoid Bodies

Materials and Methods

Cell culture: The hES H9.2 and 13 cell line and an iPS line were used. Undifferentiated hES cells were grown on mitotically inactivated mouse embryonic fibroblast (MEF) in 80% DMEM/F12 medium (Biological industries, Bet-Haaemek, Israel), 20% knockout serum replacement, 1 mM GLUTamx, 1% non-essential amino acid, 0.1 mM 2-mercaptoethanol and 4 ng/ml basic fibroblast growth factor (bFGF) (all from Gibco Invitrogen, Paisley, UK). They were then dissociated by applying 1 mg/ml type IV collagenase (Worthington Biochemical Corporation, Lakewood, N.J., USA). One hour later, the cells were transferred into plastic petri dishes (Miniplast, Ein-Shemer, Israel) in order to allow their aggregation. The resultant embryoid bodies (EBs) were cultured for 12 days in 80% Dulbeco's modified Eagle's medium, 20% knockout serum replacement, 1 mM GLUTamx, 1% non-essential amino acid (from Gibco Invitrogen), with a change of medium every three days. Two days prior to sorting, the embryoid bodies (EBs) (which consisted of 10,000 cells on average) were plated at a density of 300 EBs per well in 6-well culture plastic plates in DMEM supplemented with 20% FBS, 1 mM GLUTamx and 1% non-essential amino acid.

FACS and MACS Sorting: In order to prepare the cells for sorting, the cells were dissociated by applying 0.5 ml of TrypLE Select (Invitrogen) to each well for 15 minutes at 37° C. The cells were collected and centrifuged 1000 g×5 minutes, washed once in PBS and blocked in 1% BSA for 15 minutes in ice. After two additional washings in PBS, the cells were separated to a single cell suspension by passing through a 40 micron mesh. The cells were stained by culturing in the presence of an antibody against GLUT2 (R&D) for 30 minutes in ice, followed by 15 minutes with secondary antibody (goat anti mouse Fitc; Chemicon or goat anti mouse IgG Microbeads; Militenyi Biotec for FACS or MACS respectively).

For FACS analysis and sorting the cell pellet was incubated in PBS, 0.5% BSA and 25 mM Hepes. The cells were separated using the FACS Aria system (BD Biosciences, Bedford, Mass., USA).

For MACS sorting the cells were incubated with PBS, 0.5% BSA and 2 mM EDTA and separated according to the manufacture instructions.

Real-time RT-PCR: Total RNA from sorted and unsorted cells were isolated using the RNeasy kit (Qiagen). cDNA was synthesized using SuperScript II reverse transcriptase (Invitrogen). Real-time PCR reactions were performed with SYBR Green qPCR Supermix-UDG with ROX (Invitrogen) using primer sets listed in Table 1 herein below. Relative gene expression levels were normalized to GAPDH mRNA.

TABLE 1

| Gene | Forward primer | Reverse primer |
| --- | --- | --- |
| SOX17 | GGCGCAGCAGAATCCAGA - SEQ ID NO: 1 | CCACGACTTGCCCAGCAT - SEQ ID NO: 2 |
| CXCR4 | CACCGCATCTGGAGAACCA - SEQ ID NO: 3 | GCCCATTTCCTCGGTGTAGT - SEQ ID NO: 4 |
| PDX1 | AAGTCTACCAAAGCTCACG CG - SEQ ID NO: 5 | GTAGGCGCCGCCTGC - SEQ ID NO: 6 |
| NGN3 | GCTCATCGCTCTCTATTCTTT TGC - SEQ ID NO: 7 | GGTTGAGGCGTCATCCTTTC T - SEQ ID NO: 8 |
| PAX4 | GGGTCTGGTTTTCCAACAGAA G - SEQ ID NO: 9 | TCAGCCCTGGGAAGCA - SEQ ID NO: 10 |
| NKX2-2 | GGCCTTCAGTACTCCCTGC A - SEQ ID NO: 11 | GGGACTTGGAGCTTGAGTCC T - SEQ ID NO: 12 |
| SOX1 | ATGCACCGCTACGACATGG - SEQ ID NO: 13 | CTCATGTAGCCCTGCGAGTT G - SEQ ID NO: 14 |
| GLUT2 | AGGACTTCTGTGGACCTTATG TG - SEQ ID NO: 15 | GTTCATGTCAAAAAGCAGG G - SEQ ID NO: 16 |
| GLUT1 | ATACTCATGACCATCGCGCTA G - SEQ ID NO: 17 | AAAGAAGGCCACAAAGCCAAA TG - SEQ ID NO: 18 |
| GLUT3 | ACTTTGACGGACAAGGGAAAT G - SEQ ID NO: 19 | ACCAGTGACAGCCAACAGG - SEQ ID NO: 20 |
| FOXA2 | GGGAGCGGTGAAGATGGA - SEQ ID NO: 21 | TCATGTTGCTCACGGAGGAGT A - SEQ ID NO: 22 |
| GLUT4 | TTCCAACAGTAGGCTCCGAA G - SEQ ID NO: 23 | AAGCACCGCAGAGAACACA G - SEQ ID NO: 24 |

TABLE 1-continued

| Gene | Forward primer | Reverse primer |
| --- | --- | --- |
| TBX5 | TACCACCACACCCATCA - SEQ ID NO: 25 | ACACCAAGACAGGGACA - SEQ ID NO: 26 |
| OCT4 | CTCACCCTGGGGGTTCTAT - SEQ ID NO: 27 | CTCCAGGTTGCCTCTCTCAC T - SEQ ID NO: 28 |
| NANOG | TGAGTGTGGATCCA - SEQ ID NO: 29 | TGAATAAGCAGATC - SEQ ID NO: 30 |
| GAPDH | CCACATCGCTCAGAACCAT - SEQ ID NO: 31 | GGCAACAATATCCATTTACCA G - SEQ ID NO: 32 |

Immunofluorescence: EBs were seeded on 13 mm glass cover slides in six-well culture plates. Forty-eight hours after seeding, cell were fixed for 20 minutes in 4% paraformaldehyde in phosphate-buffered saline (PBS), permeablized using 0.5% Triton X-100 in PBS/1% serum, and incubated overnight with the primary antibodies goat anti-PDX1 (Abcame 1:1000) and mouse anti GLUT2 (R&D1:100). After rinsing, secondary anti-rabbit immunoglobulinG IgG indocarbocyanine (Cy3) conjugated antibody 1:100 and anti-mouse fluorescence isothiocyanate (FITC) conjugated antibody 1:100 (Chemicon) were added to the samples' which were then incubated for an to additional hour. Finally, the cells were rinsed once again, the nuclei of the cells were stained with TO-ORO-3 iodide 1:1000 (Molecular Probes; Leiden, Netherlands) and mounted with mounting media (Dako). The slides were analyzed using a confocal microscopy (Bio-Rad MRC 1024; Richmond, Calif.).

Protein isolation and western blot analysis: Undifferentiated hESCs and EBs at day 30 were lysed using lysis buffer. Lysates were centrifuged at 10,000 g for 10 min, and the supernatant (cytosol) was stored at −70° C. for protein quantification and Western blot analysis as previously described. The antibodies used are listed in Table 2, herein below.

TABLE 2

| Antibody | Company | Dilution Immunohistochemestry | Dilution Western Blot |
| --- | --- | --- | --- |
| Rabbit anti human Glut-1 | Alpha Diagnostic | 1:100 | 1:1000 |
| Rabbit anti human Glut-3 | Alpha Diagnostic | 1:100 | 1:1000 |
| Rabbit anti human Glut-4 | Alpha Diagnostic | 1:100 | 1:1000 |
| Mouse anti human Glut-2 | R&D | 1:100 | 1:1000 |
| Goat polyclonal PDX1 | Abcam | 1:10,000 | |

Secondary antibodies: Donkey anti goat indocarbocyanine (Cy3), donkey anti mouse Cy3, donkey anti rabbit Cy3 (all from Jackson Laboratories, West Grove, Pa.), goat anti mouse fluorescence isothiocyanate (FITC) (Chemicon). The conjugated antibodies were used as secondary antibodies and diluted 1:100.

Cellular 2-deoxyglucose uptake: Undifferentiated H9.2 cells or 10 day old EBs were seeded in 12-well plates ($1 \times 10^6$ cells/well) and cultured for 48 h. The rates of 2-deoxyglucose uptake after cells were incubated in Krebs-Ringer phosphate buffer (pH 7.4) in either the absence (basal state) or presence (insulin-stimulated state) of 10 nM insulin for 30 mM at 25 C, followed by the addition of 2-deoxy-D-2,6$^{-3}$H-glucose (Dupont NEN; Boston, Mass.) to a final concentration of 0.1 mM (1 μCi/ml) for an additional 5 mM at 25° C. Nonspecific 2-deoxyglucose uptake was measured in the presence of 20 μM cytochalasin B (Sigma) and was subtracted from each value to obtain specific uptake rates.

Results

In order to reveal the correlation between GLUT2 (NM_000340.1) and PDX1 (NM_000209.3), the expression of GLUT2, PDX1 and various other pancreatic markers were examined in differentiated embryoid bodies (EBs) using qPCR. Both GLUT2 and PDX1 expression was increased from day 14 in EBs, while GLUT2 reached maximum expression at day 19 (FIGS. 1A-D).

As expected, GLUT3 showed low expression throughout the period with increased expression on EB days 7 and 14. In contrast, GLUT1 and GLUT2 expression increased with time. GLUT4 was not detected at the protein level and was expressed in low levels at the RNA level.

To demonstrate the influence of glucose concentration on EB morphology and differentiation capacity, EBs were cultured in medium with high (25 mM) or low (5 mM) glucose levels. The expression levels of the undifferentiated marker Nanog, octamer binding transcription factor 4 (OCT4), the ectodermal marker Sex determining region Y-box 1 (SOX1), the mesodermal marker T-box transcription factor 5 (TBX5), as well as the glucose transporters GLUT 1-4, were quantified by qPCR, and were similar in both treatments (data not shown). Unlike the expression of GLUT1, GLUT3, and GLUT4, expression of GLUT2 and PDX1 was elevated in the EBs grown in medium with low glucose concentrations (FIGS. 2A-B).

Using immunofluorescence (FIG. 2C), the present inventors were able to monitor expression of GLUT1-4 in EBs. GLUT1 was visualized mainly in the outer layer of the EBs. At day 7, this isoform was localized in the cell membrane; from day 14 on, it was detected also in the cytoplasm. When the EBs were grown in medium with low glucose concentration, GLUT1 expression increased and was localized both in the membrane and in the cytoplasm.

Contrary to the mouse model in which GLUT2 was localized only in 15 and 20 day old EBs and was restricted to distinctive cells in the center of the EBs (Tonack (2006), Differentiation 74:499-509), in human EBs GLUT2 was visualized as early as day 7, and localized mostly in cell membranes in the entire EB area, with enhanced expression in the outer region. When EBs were grown in low glucose medium, cytoplasmic and overall expression of GLUT2 was elevated.

GLUT3 was visualized in the outer region of some of the EBs. In EBs grown in high glucose concentration, GLUT3 expression was low and appeared in membranes of regions of some of the EBs. In contrast, in EBs grown in low glucose medium, the number of cells expressing GLUT3 was increased; GLUT3 was noticed in the center of the EBs and in the cytoplasm as well as in the membrane.

GLUT4 was not detected in the EBs by immunofluorescence (up to 28 day-old EBs; data not shown) and Western blot (30 day-old EBs; data not shown).

Glucose uptake in differentiated and undifferentiated hESCs: Glucose transporter function was determined by the rate of cellular glucose uptake in undifferentiated hESCs and in 10 day old EBs. Cells were incubated with or without insulin (100 nM) for 30 minutes (FIG. 1E). The EB cells were more responsive to insulin stimulation, which enhanced glucose uptake by as much as 2.5 fold above the basal level. In the undifferentiated hESCs, insulin had only a minor effect on glucose uptake.

14-19 day old EBS from two hESC lines (H9.2 and I3) and from foreskin fibroblast derived iPSCs were then sorted to GLUT2 positive and GLUT2 negative populations using either FACS ARIA sorter or the MACS kit (magnetic sorting).

After sorting the cells by the FACS ARIA system, (sorted population is represented in FIG. 4D), GLUT2 and PDX1 expression were elevated in the GLUT2+ cells by more then 100 fold (FIG. 4A). In addition, those cells had elevated expression of endoderm markers. Those markers include PAX4, ngn3, CXCR4, and sox17. Sox1, an exodermal marker, was not enhanced, indicating the endodermal linage of those cells (FIGS. 4B and C).

Unlike FACS sorting, MACS does not enable gating the positive population. The result is a larger but less purified positive population. This technique is often preferred when a large number of sorted cells is required for continual growth and differentiation after sorting. Sorting the cells with the MACS kit resulted in fact in a larger but less purified GLUT2 positive population (GLUT2$^+$) with fewer enhancements of the endoderm markers. In the GLUT2$_+$ MACS sorted cells, GLUT2 was 10-30 fold higher, and PDX1 5-10 fold higher than in the GLUT2$^-$ cells. In addition, the endodermal markers PAX4, NGN3, and CXCR4 were enhanced by 5-10 fold, as shown in FIG. 5A. Fourteen to nineteen day old I3 and H9.2 EBs were sorted by MACS, and fixed and stained for the expression of membranal GLUT2. As shown in FIGS. 5B-C, GLUT2 was apparent only in the GLUT2 positive cell population, and not detected in the negative population.

Discussion

This is the first documentation of changes in expression of class I glucose transporters during the course of hESC differentiation, from the undifferentiated stage to 30 day old EBs. In addition, the present inventors examined the potential use of GLUT2 as a surface marker for the use of pancreatic progenitor cells isolation.

GLUT1 and GLUT2 expression were found to be enhanced during hESC differentiation, compared with a minor change in GLUT3 expression. GLUT4 was expressed in low levels at the RNA level and was not detected at the protein level. These results contrast with those from mouse ESCs. There, GLUT2 was detected only in EBs that were cultured for at least 15 days. Moreover, in mouse ESCs, expression of GLUT3 and GLUT4 was enhanced, with GLUT4 expression increasing with time. The differences in results between these two studies are probably due to differences in GLUT expression in mice and in humans and to variations of GLUT isoforms in different species. While GLUT1, which is responsible for basal glucose uptake, is expressed in most species and in all tissues from the oocyte stage, GLUT2 and GLUT3 appear from the 8 cell stage in mice and only from the blastocyte stage in humans.

Insulin increased glucose uptake in the EBs by 2.5 fold over control levels, but had little effect in the undifferentiated ES cells. The insulin-stimulated increase in glucose uptake was probably mediated mainly by the translocation of GLUT1, and affected in addition by increasing GLUT2 expression. Other studies have shown that in tissues predominantly expressing GLUT1, the number of GLUT1 transporters in the plasma membrane, and their activity level, determine the rate at which glucose is transported. Glucose deprivation has been shown to promote this process (19-21). In addition, GLUT1 protein and 2-deoxy-d-glucose have been shown to be up-regulated by insulin in a number of cell lines (22, 23).

Protocols for ESC differentiation generally use media containing high glucose concentrations (25 mM), based on the presumption that high glucose media is needed to maintains ESCs. The present inventors compared the response of a number of markers in differentiating EBs to low and high glucose concentration. Growing EBs in low glucose concentration increased the differentiation rates, as apparent from reduction in Nanog expression and enhanced differentiation markers such as PDX1 and GLUT2 at the RNA and protein levels. Accordingly, the use of low glucose concentration for the differentiation to definitive endoderm and pancreatic progenitors seems more applicable.

A major step in the differentiation of hESCs or iPSCs into insulin-secreting cells is the generation of cells that express pancreatic duodenal homeobox gene 1 (PDX1). The transcription factor PDX1 marks the earliest pancreatic progenitor at the onset of the earliest commitment stages towards development of the pancreas. It is expressed throughout the pancreas during the first several days of pancreatic development, as the organ grows and branches. PDX1 regulates the insulin gene and from E15.5 onwards its expression becomes mainly restricted to beta-cells (31). While several protocols have been developed to increase the proportion of PDX1 positive cells, a surface marker that correlates to the nucleic PDX1 has yet to be found. Such a marker would enable the sorting and enrichment of the pancreatic progenitor cell population, and would facilitate the development of strategies for in vitro differentiation toward insulin-producing cells.

It has been suggested that GLUT2 positive cells may be responsible for some of the differentiation of beta cells into islets after injury (4) and that GLUT2 may serve as a putative marker of pancreatic progenitor cells. Since GLUT2 is expressed in the cell membrane, it was hypothesized that it may serve as a surface marker for PDX1-expressing cells and used for sorting hESCs in the course of beta cell differentiation. In addition, the sorted cells may be directly used for transplantation and further differentiation in vivo in animal models.

Detection of a correlation in the expression pattern of PDX1 and GLUT2 led the present inventors to explore the potential use of GLUT2 as a candidate surface marker for tracking pancreatic precursor cells. In the GLUT2 sorted cells, GLUT2 and PDX1 expression were elevated in the GLUT2 positive population, as well as other endodermal markers such as PAX4, NGN3, CXCR4, and SOX17.

Using FACS, a relatively small but pure and homogeneous cell population was produced, which expressed the different pancreatic markers. In contrast, using the MACS, the sorted population was larger but less pure.

In conclusion, analyzing GLUT expression over time revealed a positive correlation between GLUT2 and PDX1 expression. Sorting the differentiated cells (either hESCs or iPSCs) for GLUT2 increased the proportion of the PDX1— expressing cell population. This simple approach may be used to differentiate embryonic stem cells and to isolate from them, using GLUT2 as a surface marker, a clean pancreatic progenitor cell population in order to reach insulin producing cells.

Example 2

Analysis of Glut2 Expression in Pluripotent Stem Cells Differentiated According to Various Protocols Materials and Methods Protocol 1: Protocol 1 was affected according to D-Amour et al [Nature Biotechnology, 2006] and Kroon et al [Nature Biotechnology, 2008] incorporated herein by reference.

Differentiation was carried out in RPMI supplemented with Glutamax and varying concentrations of FBS (0% for the first 24 hours, 0.2% for the second 24 hours and 2% for subsequent days of differentiation). The cells were cultured with 100 ng/ml activin A and 25 ng/ml Wnt3a for the first 24 hours. The cells were then ultured in RPMI with 0.2% FBS and activin at 100 ng/ml for an additional 2 days. Next, the cells were cultured with RPMI with 2% FBS and KGF (25-50 ng/ml) for 3 days. The medium was changed to DMEM with 1% B27 supplement, KAAD-cyclopamine (0.25 µM) all-trans retinoic acid (2 µM) and Noggin (50 ng/ml) for 3 days. The medium was changed to DMEM with 1% B27 for 3 days.

Protocol 2: Protocol 2 was affected according to Jiang et al, [Stem Cell, 2007] incorporated herein by reference.

Stage 1—confluent hES cells were cultured in RPMI 1640 medium with 1× B27, 4 nM activin A and 1 mM Na-butyrate for 1 day. The medium was replaced with fresh RPMI 1640/B27 medium supplemented with 4 nM activin A and 0.5 mM Na-butyrate. The cells were cultured in this medium for another six days.

Stage 2—The cells were dissociated with colagenase IV and scraped off the plate in RPMI1640/B27 medium supplemented with 20 ng/ml EGF and 100 ng/ml Noggin and transferred to ultra low attachment plates. The cells were fed with fresh medium every 2-3 days for two weeks.

Stage 3—bFGF was withheld from the cultured after two weeks and cell clusters were cultured in suspension in RPMI 1640/B27 medium supplemented with EGF and Noggin for one week.

Stage 4—cell clusters were cultured with fresh RPMI 1640 medium containing 0.5% BSA, 10 mM Nicotinamide and 50 ng/ml IGF II for 5 days and without IGF II for another 2 days.

Protocol 3: Protocol 3 was affected according to Shim J. H et al, [Diabetlogia, 2007] incorporated herein by reference.

Pancreatic differentiation was initiated by treating hEBs sequentially with serum activin and all-trans retinoic acid during EB formation. The hEBs were cultured in the presence of 20% fetal bovine serum for the first 4 days. The serum treated hEBs were then treated with 10-100 ng/ml activin A under serum free conditions for the following 6 days. The effect of retinoic acid was examined by sequential treatment of hEBs with 20% serum for 4, activin A 30 ng/ml for 4 days and retinoic acid (10 µmmol/l) for 2 days. The hEBS were then dissociated and plated at a density of 100-150 clusters per 35 mm tissue culture dish in insulin-transferrin-selenite (ITS) medium containing fibronectin (5 µg/ml).

Protocol 4: Protocol 4 was affected according to Frandsen et al, [BBRC, 2007] incorporated herein by reference.

Human embryonic stem cells were differentiated as embryoid bodies as described in Example 1. Activin B (50 ng/ml) was added to the embryoid bodies for two weeks.

Protocol 5: Protocol 5 was affected according to Tateish et al, [JBC, 2008] incorporated herein by reference.

Differentiation of embryonic stem cells was initiated in RPMI 1640 supplemented with B27 and 4 nM activin A for 7 days. Sodium butyrate was added on day 1 at a final concentration of 0.1 mM (stage 1). After stage 1, the cell were dissociated with collagenase IV and transferred into ultra low attachment plates. The cell aggregates were cultured in RPMI 1640 supplemented with B27, 20 ng/ml epidermal growth factor, 2 ng/ml basic fibroblast growth factor and 100 ng/ml noggin for 2 weeks (stage 2). At stage 3, cell clusters were cultured in suspension in RPMI 1640 supplemented with B27, 20 ng/ml epidermal growth factor and 100 ng/ml Noggin for 1 week. Finally, the cells were incubated in RPMI 1640 medium with 0.5% bovine serum albumin, 10 mM nicotinamide and 50 ng/ml insulin like growth factor II for another 2 days (stage 4).

Protocol 6: Protocol 6 was affected according to Gao et al, [Translational Research, 2008] incorporated herein by reference.

Differentiation was effected according to the chart displayed in FIG. 5.

Protocol 7: Protocol 7 was affected according to Chen et al, [Nature Chemical Biology, 2009] incorporated herein by reference.

To generate definitive endoderm population, hESCs (H9.2) were cultured on MEF feeder cells until 80-90% confluent, then treated with 25 ng/ml Wnt3a(R&D), 100 ng/ml activin A (R&D) in advanced RPMI (Invitrogene) supplemented with 1x L-glutamine for 1d then 100 ng/ml activin A in advanced RPMI supplemented with 1XL-glutamine and 0.2% (v/v) fetal bovine serum (FBS, Bethaemek). The medium was changed 2 d later to 50 ng/ml FGF10 (R&D), 0.25 mM KAAD-cyclopamine (Sigma) in advanced RPMI supplemented with 1x L-glutamine and 2% FBS and maintainned for an additional 2 d. Cells were then transferred to 50 ng/ml FGF10, 0.25 µM KAAD cyclopamine, 2 µM retinoic acid (Sigma) in DMEM supplemented with 1XL-glutamine and 1XB27 (Invitrogen) and cultured for an additional 4 d with or without 300 nM ILV (Axxora). For additional differentiation the cells were cultured for 6 d in DMEM supplemented with 1x L-glutamine, 1% B27, 50 ng/ml exendin (Sigma) and 10 µM DAPT (Sigma). At the final stage the cells were cultured for 6 d in CMRL (Invitrogen) supplemented with 1XL-glutamin, 1% B27, 50 ng/ml HGF (Bet-Haemek) and 50 ng/ml IGF (Bet-Haemek).

Protocol 8: Protocol 8 was affected according to Borowiak et al, [Cell stem cells 2009] incorporated herein by reference.

Protocol 9: Protocol 9 was affected according to Johannesson M et al, [PLOS 2009] incorporated herein by reference.

For differentiation, the cells were grown until confluence. The medium was changed to activin A 100 ng/ml and Wnt3A 25 ng/ml in RPMI 1640 supplemented with no FBS for the first day and 0.2% FBS the second and third day. On days four to seven to RPMI 1640 was supplemented with 2% FBS and from day eight DMEM was supplemented with 2% FB S. From day four onward, FGF4 (1.1 ng/ml) and retinoic acid (2 µM) were added.

Real-time PCR: Quantification of markers was performed as described for Example 1.

Results

The amount of GLUT2 (and additional markers) following differentiation according to the described protocols is illustrated in FIGS. 7-10.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of generating GLUT2-expressing cells the method comprising:
   (a) differentiating human stem cells under conditions such that at least a portion of said cells express glucose transporter 2 (GLUT2) on a membrane of said cells so as to generate GLUT2-expressing cells; and
   (b) isolating from said cells resultant of step (a) GLUT2-expressing cells using an anti GLUT2 antibody which binds to said GLUT2 expressed on said membrane so as to generate a population of GLUT2 enriched cells, wherein at least 80% of said population of GLUT2 enriched cells express GLUT2, thereby generating GLUT2-expressing cells.

2. The method of claim 1, wherein said isolating is effected by a fluorescence-activated cell sorter (FACS).

3. The method of claim 1, wherein said human stem cells comprise human embryonic stem cells.

4. The method of claim 1, wherein said stem cells comprise induced pluripotent stem cells.

5. The method of claim 1, wherein said human stem cells comprise human pluripotent stem cells.

6. The method of claim 1, wherein said differentiating said human stem cells is effected by generating embryoid bodies.

7. The method of claim 6, wherein said embryoid bodies are 14 day old.

8. The method of claim 6, wherein said embryoid bodies 14-25 day old.

9. The method of claim 6, wherein said embryoid bodies are 14-19 day old.

10. The method of claim 1, wherein said conditions comprise a glucose concentration of less than 5 mM.

11. The method of claim 1, wherein said isolating is effected by a magnetic-activated cell sorting (MACS).

12. The method of claim 1, further comprising:
   (c) differentiating said population of GLUT2 enriched cells into insulin-producing cells.

* * * * *